United States Patent
Kim

(10) Patent No.: US 11,116,822 B2
(45) Date of Patent: Sep. 14, 2021

(54) METHOD FOR TREATMENT OF LIVER STEATOSIS OR NON-ALCOHOLIC FATTY LIVER BY USING 2-MONOACYLGLYCEROL CLEAVING ENZYME

(71) Applicant: INDUSTRY-ACADEMIC COOPERATION FOUNDATION, YONSEI UNIVERSITY, Seoul (KR)

(72) Inventor: Jae Woo Kim, Seoul (KR)

(73) Assignee: INDUSTRY-ACADEMIC COOPERATON FOUNDATION, YONSE: UNIVERSITY, Seoul (KR)

( * ) Notice: Subject to any disclaimer, the term of this patent is extended or adjusted under 35 U.S.C. 154(b) by 270 days.

(21) Appl. No.: 16/318,258

(22) PCT Filed: Jul. 14, 2017

(86) PCT No.: PCT/KR2017/007585
§ 371 (c)(1),
(2) Date: Mar. 27, 2019

(87) PCT Pub. No.: WO2018/016806
PCT Pub. Date: Jan. 25, 2018

(65) Prior Publication Data
US 2019/0351030 A1    Nov. 21, 2019

(30) Foreign Application Priority Data
Jul. 19, 2016  (KR) .................. 10-2016-0091606

(51) Int. Cl.
| | | |
|---|---|---|
| A23L 33/18 | (2016.01) | |
| A61K 38/46 | (2006.01) | |
| A61P 1/16 | (2006.01) | |
| A61P 3/04 | (2006.01) | |
| A61P 3/06 | (2006.01) | |
| A61P 3/10 | (2006.01) | |

(52) U.S. Cl.
CPC .......... *A61K 38/465* (2013.01); *A23L 33/18* (2016.08); *A61P 1/16* (2018.01); *A61P 3/04* (2018.01); *A61P 3/06* (2018.01); *A61P 3/10* (2018.01); *C12Y 301/01023* (2013.01); *A23V 2002/00* (2013.01)

(58) Field of Classification Search
CPC combination set(s) only.
See application file for complete search history.

(56) References Cited

U.S. PATENT DOCUMENTS 9,375,461 B2 * 6/2016 Rombi .................. A61P 3/04

FOREIGN PATENT DOCUMENTS

KR    2014-0068243    6/2014

OTHER PUBLICATIONS

Hall et al., "Evidence for Regulated Monoacylglycerol Acyltransferase Expression and Activity in Human Liver" *Journal of Lipid Research*, 2012, 53:990-999.
International Search Report and Written Opinion issued in International Patent Application No. PCT/KR2017/007585, dated Nov. 20, 2017.
Saponaro et al., "The Subtle balance between Lipolysis and Lipogenesis: a Critical Point in Metabolic Homeostasis" *Nutrients*, 2015, 7:9453-9474.
Schweitzer et al., "Targeting Hepatic Glycerolipid Synthesis and Turnover to Treat Fatty Liver Disease" *Advances in Hepatology*, 2014, Article ID 498369.

* cited by examiner

*Primary Examiner* — Heidi Reese
(74) *Attorney, Agent, or Firm* — Norton Rose Fulbright US LLP

(57) ABSTRACT

The present invention relates to a method for treating liver steatosis or non-alcoholic fatty liver by using a 2-monoacylglycerol degrading enzyme. More particularly, the present invention provides a method for treating metabolic syndrome such as liver steatosis, non-alcoholic fatty liver, hyperlipidemia, type 2 diabetes, and/or obesity by using a 2-monoacylglycerol degrading enzyme, in which the 2-monoacylglycerol degrading enzyme completely degrades triglyceride into fatty acids and glycerol in a digestive tract such that fat absorption is delayed and blood absorption of triglyceride is decreased, and in which, in a case where monoacylglycerol is degraded by a monoacylglycerol lipase in a digestive tract, although degraded products of the monoacylglycerol are absorbed into digestive epithelial cells, recombination thereof into triglyceride in the digestive epithelial cells is delayed or energy consumption is promoted during this process.

20 Claims, 27 Drawing Sheets
Specification includes a Sequence Listing.

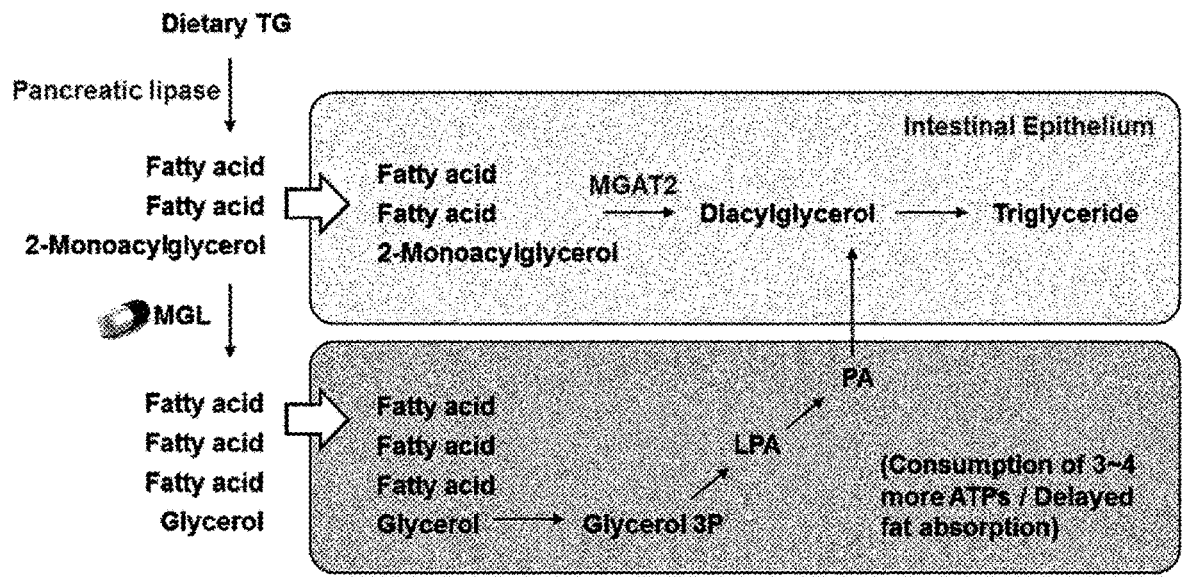

FIG. 3

MGL GenBank Number
    human mRNA NM_001003794, protein Q99685
    mouse mRNA NM_011844, protein O35678

Human MGL
MPEESSPRRTPQSIPYQDLPHLVNADGQYLFCRYWKPTGTPKALIFVSHGAGEHSGRYEE
LARMLMGLDLLVFAHDHVGHGQSEGERMVVSDFHVFVRDVLQHVDSMQKDYPGLPVFLLG
HSMGGAIAILTAAERPGHFAGMVLISPLVLANPESATTFKVLAAKVLNLVPNLSLGPID
SSVLSRNKTEVDIYNSDPLICRAGLKVCFGIQLLNAVSRVERALPKLTVPFLLQGSADR
LCDSKGAYLLMELAKSQDKTLKIYEGAYHVLHKELPEVTNSVFHEINMWVSQRTATAGTA
SPP (SEQ ID NO: 7)

Mouse MGL
MPEASSPRRTPQNVPYQDLPHLVNADGQYLFCRYWKPSGTPKALIFVSHGAGEHCGRYDE
LAHMLKGLDMLVFAHDHVGHGQSEGERMVVSDFQVFVRDVLQHVDTIQKDYPDVPIFLLG
HSMGGAISILVAAERPTYFSGMVLISPLVLANPESASTLKVLAAKLLNFVLPNMTLGRID
SSVLSRNKSEVDLYNSDPLVCRAGLKVCFGIQLLNAVARVERAMPRLTLPFLLQGSADR
LCDSKGAYLLMESSRSQDKTLKMYEGAYHVLHRELPEVTNSVLHEVNSWVSHRIAAAGAG
CPP (SEQ ID NO: 8)

Human and mouse MGL positivity 93.4%, identity 84.2%

FIG. 4

6-week-old
Sigma, L3126
Lipase from porcine pancreas
1, 3-specific lipase
Sigma, L1754
Lipase from Candida rugosa
non-specific lipase
gavage 2,000 units, daily, total 7 weeks
FIG. 8
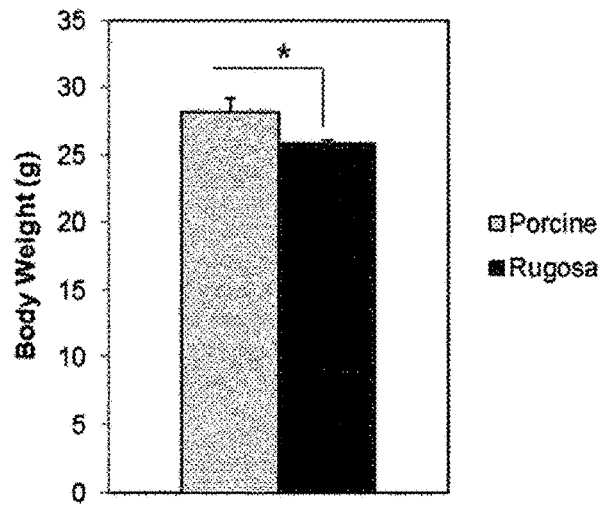
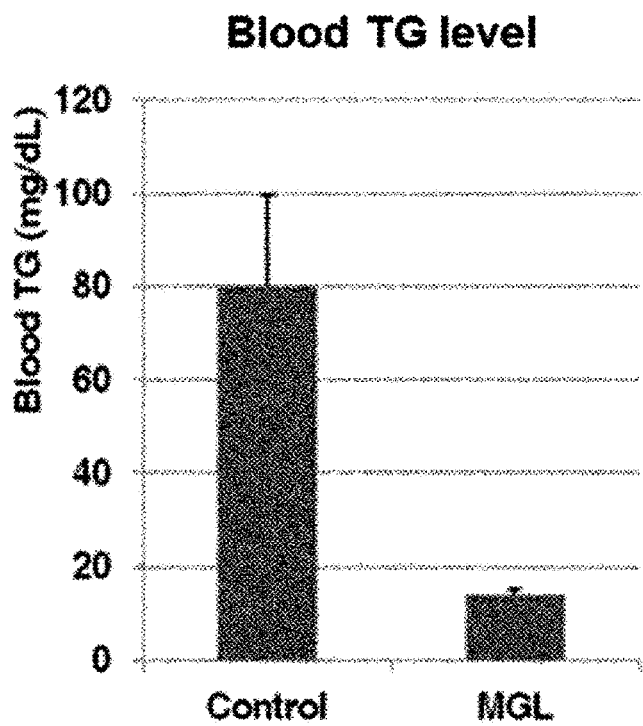
FIG. 9

METHOD FOR TREATMENT OF LIVER STEATOSIS OR NON-ALCOHOLIC FATTY LIVER BY USING 2-MONOACYLGLYCEROL CLEAVING ENZYME

CROSS-REFERENCE TO RELATED APPLICATIONS

This application is a national phase application under 35 U.S.C. § 371 of International Application No. PCT/KR2017/007585, filed Jul. 14, 2017, which claims priority to and the benefit of Korean Patent Application No. 10-2016-0091606, filed Jul. 19, 2016. The contents of the referenced patent applications are incorporated into the present application by reference.

FIELD OF THE DISCLOSURE

The present invention relates to a method for treating liver steatosis or non-alcoholic fatty liver by using a 2-monoacylglycerol degrading enzyme. More particularly, the present invention provides a method for treating metabolic syndrome such as liver steatosis, non-alcoholic fatty liver, hyperlipidemia, type 2 diabetes, and/or obesity by using a 2-monoacylglycerol degrading enzyme, in which the 2-monoacylglycerol degrading enzyme completely degrades triglyceride into fatty acids and glycerol in a digestive tract such that fat absorption is delayed and blood absorption of triglyceride is decreased, and in which, in a case where monoacylglycerol is degraded by a monoacylglycerol lipase in a digestive tract, although degraded products of the monoacylglycerol are absorbed into digestive epithelial cells, recombination thereof into triglyceride in the digestive epithelial cells is delayed or energy consumption is promoted during this process.

BRIEF DESCRIPTION OF RELATED ART

Recently, due to economic development and changes in eating habit or the like, development of metabolic syndrome-related diseases including various diseases such as obesity, hyperlipidemia, hypertension, arteriosclerosis, hyperinsulinemia, type 2 diabetes, liver steatosis, and non-alcoholic fatty liver has been rapidly increasing. These diseases may separately develop. However, in most cases, such diseases generally develop with several symptoms while being closely related to one another.

Obesity is a disease group that most strongly threatens health of modern people. High-level obesity decreases insulin sensitivity and causes many metabolic changes in a body, which in turn causes many complications in the vascular system, the nervous system, or the like, thereby leading to death. Therefore, in medical communities, it is considered very important to develop a lifestyle that can decrease obesity or a therapeutic drug for obesity.

Obesity results from an imbalance between energy intake and energy use. First, a center for energy intake is located in hypothalamus of the brain, and the energy intake is regulated by hormones such as leptin and ghrelin in a body. Nutrients that have been once ingested and absorbed in a digestive tract are never excreted. Such nutrients are used as energy or stored in a body. Therefore, in treatment of obesity, efforts have been made to develop an obesity suppressant with a mechanism that suppresses energy intake, and an appetite suppressant such as Furing and Reductile is used.

Another method of decreasing energy intake is a method of suppressing absorption of fat in a digestive tract. A drug using this method is Xenical. Xenical is a drug that suppresses lipase which is a lipolytic enzyme in the pancreas. In a case where Xenical is administered, triglyceride is not absorbed in a digestive tract due to not being degraded, and is excreted in feces.

A second method is to increase energy use. A common way people cope with obesity is to "eat less and exercise more". Thus, doing more exercise to increase energy consumption can be regarded as a reliable therapy for obesity. Recently, various efforts have been made to promote energy consumption by drugs, and studies have been conducted in order to promote energy consumption by increasing expression of uncoupling proteins which are mainly present in brown fat.

However, in a case of methods for suppressing appetite, most drugs act on the central nervous system, and thus are often inevitably accompanied by nervous system side effects. Also, decreased appetite has a problem that can be accompanied by depression. In a case of Xenical that suppresses lipolysis in a digestive tract, patients are reluctant to take medication due to fatty stool and corresponding odors. Also, Xenical causes inconvenience in social life due to a problem of controlling inclination for stool. A method of promoting energy consumption by applying an uncoupling protein is still at a development stage, and it is difficult to use such a method for humans until drug specificity according to distinctiveness of each organ is secured.

In addition, as commercially available anti-obesity agents, thiazolidinediones (TZDs), Xenical (Roche Korea Co., Ltd.), sibutramine, and the like are mentioned. It has been reported that these drugs have side effects such as cardiovascular actions, central nervous system actions, hepatic disorders, and renal disorders. Therefore, there is an urgent need to develop a high value-added, multi-functional product which has no side effects at a later time due to long-term ingestion and is used for both prevention and treatment of obesity.

Meanwhile, it is known that a monoacylglycerol lipase (MGL) degrades monoacylglycerol to form a free fatty acid and glycerol. In the prior art, it has been reported that increased expression of the monoacylglycerol lipase in intestines leads to an overeating-induced obesity phenotype (Chon, et al., FASEB, 22: 807, 2008), and it has been reported that suppression of the monoacylglycerol lipase is useful for treatment of pain, inflammation, and a central nervous system (CNS) disorder (Schlossburg et al., Nat. Neurosci., 13 (9): 1113, 2010). These study reports all relate to phenomena appearing in a case where the monoacylglycerol lipase acts in cells in a body. There is no report for a case where the monoacylglycerol lipase acts in a digestive tract, and no monoacylglycerol lipase activity is found in a human digestive tract.

SUMMARY OF THE INVENTION

Accordingly, the present invention is based on an idea that a 2-monoacylglycerol degrading enzyme can be used as a prophylactic or therapeutic agent for liver steatosis, non-alcoholic fatty liver, hyperlipidemia, type 2 diabetes, and/or obesity in view of the fact that in a case where a monoacylglycerol lipase is caused to act in a digestive tract, the monoacylglycerol lipase completely degrades triglyceride into fatty acids and glycerol in the digestive tract such that fat absorption can be delayed and blood absorption of triglyceride can be decreased, and in a case where 2-monoacylglycerol is degraded by the monoacylglycerol lipase in a digestive tract, although degraded products of the 2-monoacylglycerol are absorbed into digestive epithelial cells, recombination thereof into triglyceride in the digestive epithelial cells can be delayed and energy consumption can be promoted during this process. The present invention has been completed by demonstrating the above idea.

The present invention has been made to solve the above problems. An object of the present invention is to provide a method for treating liver steatosis, non-alcoholic fatty liver, hyperlipidemia, type 2 diabetes, and/or obesity by using a 2-monoacylglycerol degrading enzyme.

Another object of the present invention is to provide a composition for prevention, amelioration, or treatment of liver steatosis, non-alcoholic fatty liver, hyperlipidemia, type 2 diabetes, and/or obesity, comprising a 2-monoacylglycerol degrading enzyme.

In order to solve the above-mentioned problems, the present invention provides a method for treating liver steatosis or non-alcoholic fatty liver by using a monoacylglycerol-degrading enzyme.

In addition, the present invention provides a method for treating hyperlipidemia or type 2 diabetes by using a monoacylglycerol degrading enzyme.

In addition, the present invention provides a method of treating obesity by using a monoacylglycerol degrading enzyme.

In addition, the present invention provides a pharmaceutical composition for prevention or treatment of liver steatosis or non-alcoholic fatty liver, comprising a monoacylglycerol degrading enzyme; and a functional health food composition for prevention or amelioration of liver steatosis or non-alcoholic fatty liver, comprising a monoacylglycerol degrading enzyme.

In addition, the present invention provides a pharmaceutical composition for prevention or treatment of hyperlipidemia or type 2 diabetes, comprising a 2-monoacylglycerol degrading enzyme; and a functional health food composition for prevention or amelioration of hyperlipidemia or type 2 diabetes, comprising a 2-monoacylglycerol degrading enzyme.

In addition, the present invention provides a pharmaceutical composition for prevention or treatment of obesity, comprising a 2-monoacylglycerol degrading enzyme; and a functional health food composition for prevention or amelioration of obesity, comprising a 2-monoacylglycerol degrading enzyme.

According to a embodiment of the present invention, the 2-monoacylglycerol degrading enzyme may be a lipase that specifically or non-specifically degrades 2-monoacylglycerol. Preferably, the 2-monoacylglycerol degrading enzyme may be a lipase that specifically degrades 2-monoacylglycerol.

According to another preferred embodiment of the present invention, the lipase that specifically degrades 2-monoacylglycerol may be a 2-position specific lipase derived from any one selected from the group consisting of human, mouse, yeast, fungi, and bacteria.

According to yet another preferred embodiment of the present invention, the 2-position specific lipase may consist of the amino acid sequence of SEQ ID NO: 7 or 8.

According to still yet another preferred embodiment of the present invention, the 2-position specific lipase may be expressed by a recombinant vector that contains the base sequence of SEQ ID NO: 5 or 6.

According to still yet another preferred embodiment of the present invention, the 2-position specific lipase may be produced by a strain transformed with the recombinant vector.

According to still yet another embodiment of the present invention, the lipase that non-specifically degrades 2-monoacylglycerol may be a positional non-specific lipase derived from any one selected from the group consisting of yeast, fungi, and bacteria.

According to still yet another preferred embodiment of the present invention, the 2-monoacylglycerol degrading enzyme may completely degrade 2-monoacylglycerol into a fatty acid and glycerol such that an amount of 2-monoacylglycerol to be absorbed into digestive epithelial cells is decreased.

According to still yet another preferred embodiment of the present invention, the 2-monoacylglycerol degrading enzyme may completely degrade 2-monoacylglycerol into a fatty acid and glycerol, energy consumption may increase due to a process by which the degraded fatty acid and glycerol are absorbed into digestive epithelial cells and re-synthesized into triglyceride, and the increase in energy consumption may be caused by consumption of three or four more ATPs as compared with a process by which monoacylglycerol and fatty acids are re-synthesized into triglyceride in the digestive epithelial cells.

The present invention provides a use of a 2-monoacylglycerol degrading enzyme for the manufacture of a medicament for treatment of liver steatosis, non-alcoholic fatty liver, hyperlipidemia, type 2 diabetes, and/or obesity.

The composition of the present invention comprising a 2-monoacylglycerol degrading enzyme has effects of delaying fat absorption and decreasing blood absorption of triglyceride by completely degrading triglyceride into fatty acids and glycerol in a digestive tract. In a case where 2-monoacylglycerol is degraded by a 2-monoacylglycerol degrading enzyme in the digestive tract, although degraded products of the 2-monoacylglycerol are absorbed into digestive epithelial cells, recombination thereof into triglyceride in the digestive epithelial cells can be delayed or energy consumption can be promoted during this process. Therefore, such a composition can be utilized for medical products and functional health foods for prevention, amelioration, or treatment of liver steatosis, non-alcoholic fatty liver, hyperlipidemia, type 2 diabetes, and/or obesity, and the like.

BRIEF DESCRIPTION OF THE DRAWINGS

FIG. 3 is a schematic diagram, illustrating a pathway in which, after digestion of triglyceride, fat absorbed into digestive epithelial cells is re-synthesized into triglyceride. In the presence of a monoacylglycerol lipase (MGL), triglyceride is completely degraded into three fatty acids and glycerol, and thus more energy is consumed to re-form the triglyceride in the digestive epithelial cells.

FIG. 4 illustrates GenBank Numbers and amino acid sequences of human and mouse monoacylglycerol lipases (MGLs).

In FIG. 6, 1 denotes a protein before dialysis, and 2 denotes a protein after dialysis.

FIG. 8 graphically illustrates changes in body weight after administering a porcine pancreatic lipase (control group) and a *Candida rugosa* lipase (experimental group), respectively, into 6-week-old mice for 7 weeks.

FIG. 9 is data, illustrating changes in blood triglyceride concentration caused by monoacylglycerol lipase (MGL) in mice into which olive oil has been administered.

DETAILED DESCRIPTION OF THE INVENTION

Figure 1:
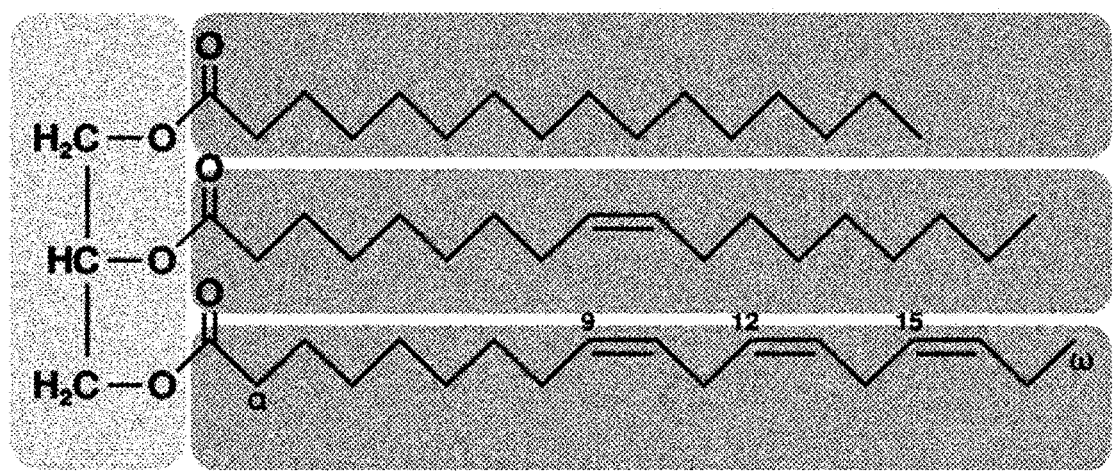
FIG. 1 is a schematic diagram, illustrating a structure of triglyceride.

Hereinafter, the present invention will be described in more detail.

As described above, drugs used as therapeutic agents for liver steatosis, non-alcoholic fatty liver, hyperlipidemia, type 2 diabetes, and/or obesity have problems of causing side effects such as a heart disease, a respiratory disease, an increase in blood pressure, and insomnia, and exhibiting short efficacy duration. Therefore, there is an urgent need to develop a high value-added, multi-functional product which has no side effects at a later time, and not only has prophylactic and therapeutic effects on metabolic syndrome but also has prophylactic effects on various diseases due to decreased oxidative stress.

Accordingly, in the present invention, a solution to the above-mentioned problems has been sought by providing a composition for prevention, amelioration, and/or treatment of liver steatosis or non-alcoholic fatty liver, comprising a 2-monoacylglycerol degrading enzyme, and a method for treating liver steatosis or non-alcoholic fatty liver by using the 2-monoacylglycerol degrading enzyme. The composition provided in the present invention has effects of delaying fat absorption and decreasing blood absorption of triglyceride by completely degrading triglyceride into fatty acids and glycerol in a digestive tract. Thus, the composition can be utilized for medical products and functional health foods for preventing, ameliorating, or treating liver steatosis, non-alcoholic fatty liver, hyperlipidemia, type 2 diabetes, and/or obesity.

Obesity increases blood pressure and blood glucose, increases blood triglyceride, and decreases HDL cholesterol. As a result, obesity can lead to increased risk of metabolic syndrome, and ultimately to increased risk of a cardiovascular disease. The metabolic syndrome refers to simultaneous occurrence of abdominal obesity, diabetes, dyslipidemia (increased triglyceride and decreased high-density cholesterol), hypertension, and the like in one person. That is, the composition of the present invention comprising a 2-monoacylglycerol degrading enzyme can be used as a prophylactic or therapeutic agent for liver steatosis, non-alcoholic fatty liver, hyperlipidemia, type 2 diabetes, and/or obesity. Thus, the composition can be used as a therapeutic agent for lipid-related metabolic syndrome diseases.

The monoacylglycerol lipase can decrease blood triglyceride. In a case where the monoacylglycerol lipase is present in intestines, 2-monoacylglycerol is completely degraded into a fatty acid and glycerol, which makes it possible to delay a process by which monoacylglycerol and fatty acids are absorbed into digestive epithelial cells and re-synthesized into triglyceride.

In addition, 2-monoacylglycerol is completely degraded into a fatty acid and glycerol by the 2-monoacylglycerol degrading enzyme, energy consumption increases due to a process by which the degraded fatty acid and glycerol are absorbed into digestive epithelial cells and re-synthesized into triglyceride, and the increase in energy consumption may be caused by consumption of three or four more ATPs as compared with a process by which monoacylglycerol and fatty acids are re-synthesized into triglyceride in the digestive epithelial cells.

The present invention is drawn from a paradoxical idea that focuses on characteristics of a nutrient absorption and metabolic pathway in a digestive tract, and is based on a mechanism that further promotes digestion of triglyceride in the digestive tract, thereby decreasing fat absorption and promoting energy consumption.

As illustrated in FIG. 1, triglyceride has a form in which three fatty acids are bound to glycerol. A representative enzyme that degrades triglyceride in a human digestive tract is lipase which is secreted in the pancreas. However, the lipase is an incomplete lipase which degrades fatty acids at positions 1 and 3 but does not liberate a fatty acid bound at position 2. Eventually, products caused by this enzyme are present as two fatty acids and one monoacylglycerol.

Figure 2:
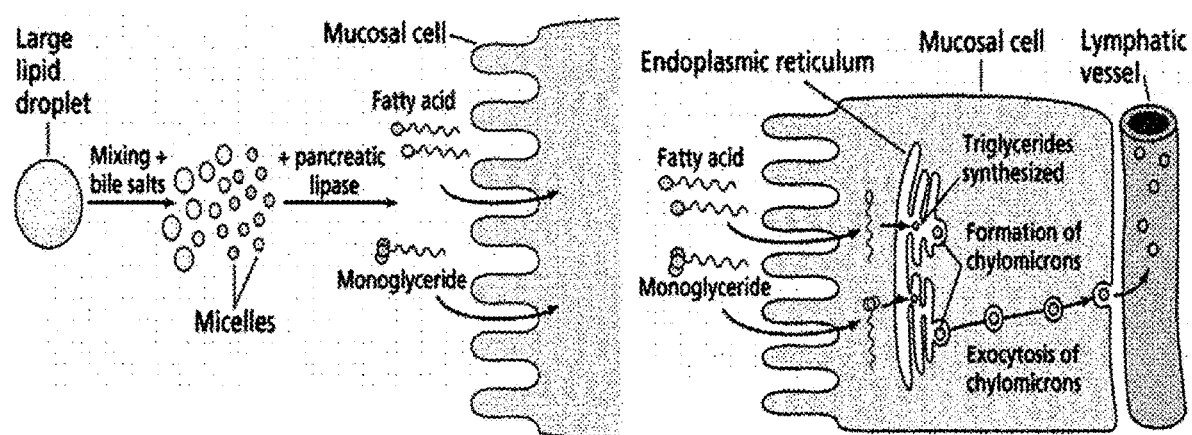
FIG. 2 is a schematic diagram, illustrating a digestion and absorption process of triglyceride in a digestive tract. Two fatty acids and monoacylglycerol, which are degraded products caused by a pancreatic lipase, are absorbed into digestive epithelial cells and are recombined again into triglyceride in the digestive epithelial cells. The triglyceride is liberated into a lymphatic system in the form of chylomicron.

FIG. 2 is a schematic diagram, illustrating a digestion and absorption process of triglyceride in a digestive tract. Two fatty acids and monoacylglycerol, which are degraded products caused by a pancreatic lipase, are absorbed into digestive epithelial cells and are recombined again into triglyceride in the digestive epithelial cells. The triglyceride is liberated into a lymphatic system in the form of chylomicron.

An enzyme called MGAT2, which is present in the digestive epithelial cells, acts in a process by which the two fatty acid and monoacylglycerol are combined into triglyceride. As illustrated in the upper part of FIG. 3, the enzyme attaches one fatty acid to monoacylglycerol such that diacylglycerol is formed, and the formed diacylglycerol immediately becomes triglyceride. After re-forming triglyceride in this manner, the triglyceride has to form lipoprotein in the form of chylomicron such that the triglyceride can be secreted into a lymphatic system or vascular system and circulated in a state of being dissolved.

As illustrated in the lower part of FIG. 3, in a case where an assumption that a monoacylglycerol lipase is used to degrade 2-monoacylglycerol into a fatty acid and glycerol is made in the above metabolic pathway, a pathway that re-forms triglyceride eventually changes. Glycerol needs to be phosphorylated through energy consumption, and two fatty acids are attached thereto such that a phosphatidic acid is formed. Then, a phosphoric acid is detached and diacylglycerol is formed. Triglyceride can be re-formed in such a process. For the above process, three to four more ATPs are consumed as compared with a process by which 2-monoacylglycerol directly forms triglyceride, thereby promoting energy consumption and making it possible to prevent or treat obesity.

That is, in the present invention, the 2-monoacylglycerol degrading enzyme is intended to be used for treatment of liver steatosis, non-alcoholic fatty liver, hyperlipidemia, type 2 diabetes, and/or obesity, in which the 2-monoacylglycerol degrading enzyme is orally taken to completely degrade triglyceride into fatty acids and glycerol in a digestive tract, thereby delaying fat absorption and re-formation, and promoting energy consumption.

Accordingly, the present invention provides a method for treating liver steatosis or non-alcoholic fatty liver by using the 2-monoacylglycerol degrading enzyme; a pharmaceutical composition for prevention or treatment of liver steatosis or non-alcoholic fatty liver, comprising the 2-monoacylglycerol degrading enzyme; or a functional health food composition for prevention or amelioration of liver steatosis or non-alcoholic fatty liver, comprising the 2-monoacylglycerol degrading enzyme.

In addition, the present invention provides a method for treating hyperlipidemia or type 2 diabetes by using the 2-monoacylglycerol degrading enzyme; a pharmaceutical composition for prevention or treatment of hyperlipidemia or type 2 diabetes, comprising the 2-monoacylglycerol degrading enzyme; or a functional health food composition for prevention or amelioration of hyperlipidemia or type 2 diabetes, comprising the 2-monoacylglycerol degrading enzyme.

In addition, the present invention provides a method for treating obesity by using the 2-monoacylglycerol degrading enzyme; a pharmaceutical composition for prevention or treatment of obesity, comprising the 2-monoacylglycerol degrading enzyme; or a functional health food composition for prevention or amelioration of obesity, comprising the 2-monoacylglycerol degrading enzyme.

In the method or composition of the present invention, the 2-monoacylglycerol degrading enzyme can be used without limitation as long as the 2-monoacylglycerol degrading enzyme can completely degrade 2-monoacylglycerol into a fatty acid and glycerol. Preferably, the 2-monoacylglycerol degrading enzyme may be a lipase that specifically degrades 2-monoacylglycerol.

An origin of the lipase that specifically degrades 2-monoacylglycerol is not particularly limited, and may be, for example, a 2-position-specific lipase derived from any one selected from the group consisting of human, mouse, yeast, fungi, and bacteria.

As used herein, the term "2-position specific lipase" refers to a lipase that exhibits reaction specificity only to a fatty acyl group at 2-position of triglyceride.

In a preferred embodiment of the present invention, in order to produce the 2-position specific lipase, a human- or mouse-derived monoacylglycerol lipase (MGL) gene sequence was introduced into a recombinant vector, and a monoacylglycerol lipase protein was caused to be expressed using an *E. coli* system capable of expressing a large amount of the protein. The protein was partially purified. A His-tag was used to facilitate purification of the target protein. However, in addition to the human- or mouse-derived gene sequence, any gene sequence encoding a 2-position specific lipase can be used without limitation.

FIG. 4 illustrates the GenBank Numbers and amino acid sequences of human and mouse monoacylglycerol lipases (MGLs). If necessary, the amino acid sequence of the human or mouse-derived monoacylglycerol lipase as illustrated in FIG. 4 can be partially modified to increase enzymatic activity, and a base sequence of the monoacylglycerol lipase can be partially modified to increase production of monoacylglycerol in a recombinant microorganism.

Figure 5:
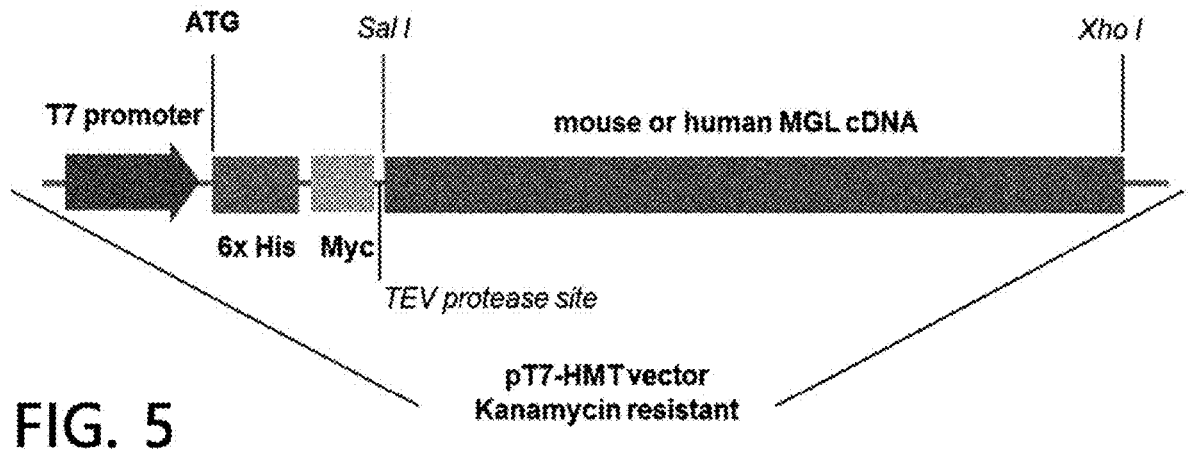
FIG. 5 illustrates a bacterial expression vector system produced for mass production of a monoacylglycerol lipase (MGL).
Figure 6:
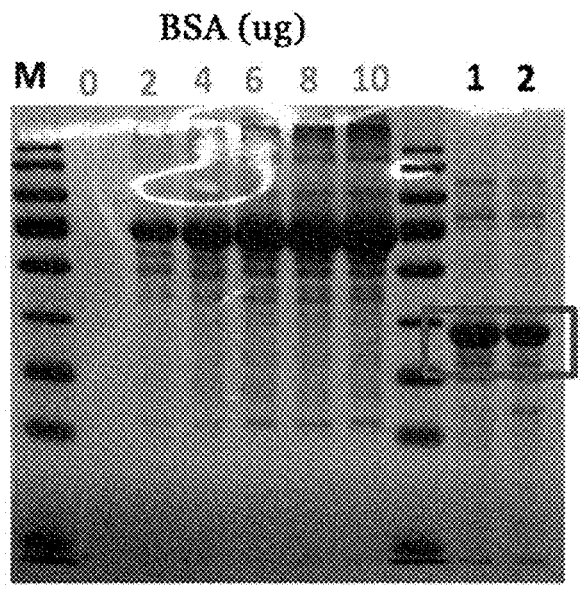
FIG. 6 is data, illustrating results obtained by performing SDS-PAGE after isolation and purification of a monoacylglycerol lipase (MGL).
Figure 7:
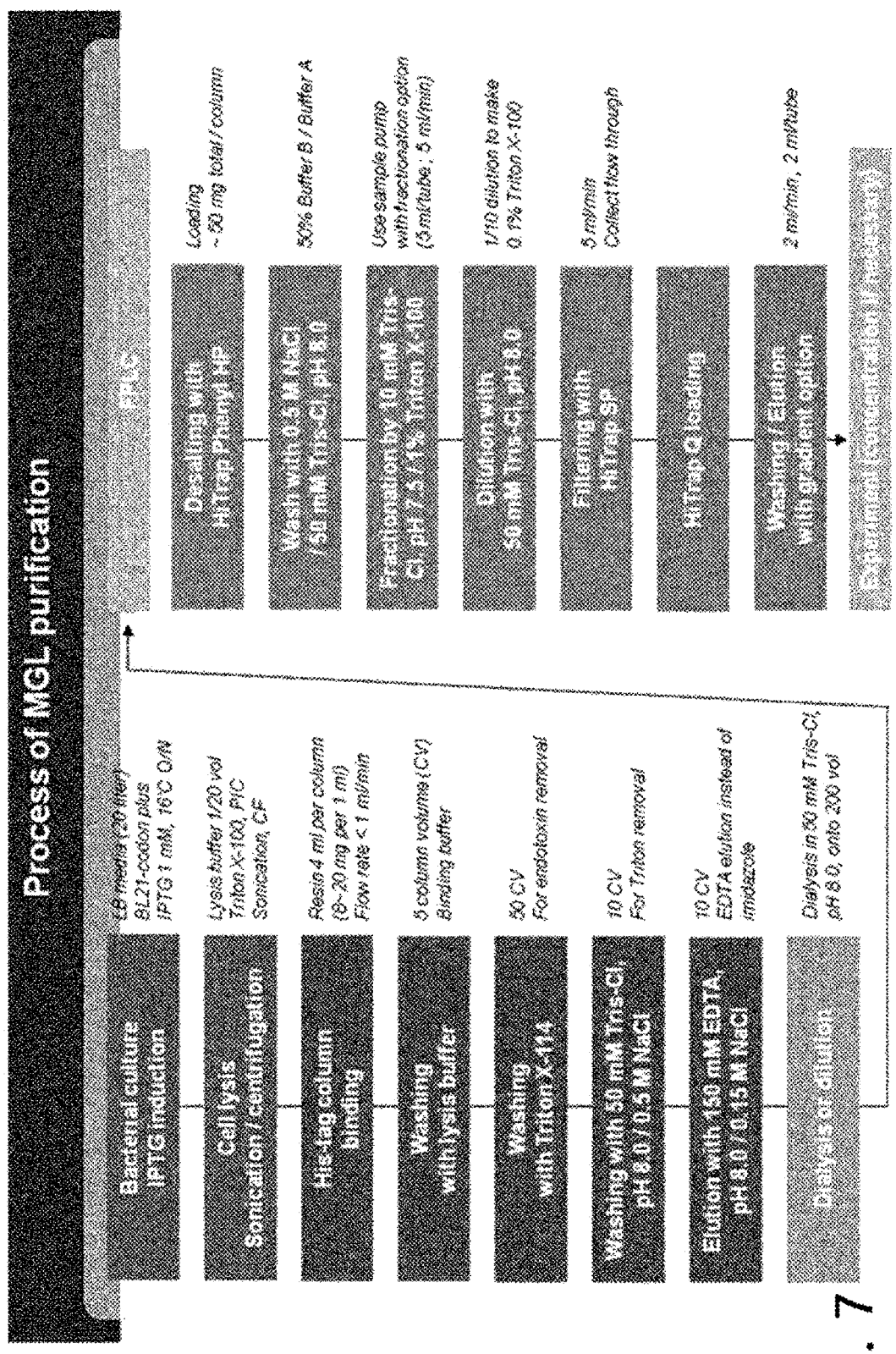
FIG. 7 is a schematic diagram, illustrating a process for pure isolation and purification of a monoacylglycerol lipase (MGL).

FIG. 5 illustrates a bacterial expression vector system produced for mass production of a monoacylglycerol lipase (MGL). This bacterial expression vector system was used to perform mass production of the protein, and then an examination was performed. As a result, as illustrated in FIG. 6, isolation of the monoacylglycerol lipase (MGL) was successfully performed. A column purification process for pure isolation of the monoacylglycerol lipase led to creation of a protein mass-production process specific to this protein, which is illustrated in FIG. 7.

In the composition of the present invention, an origin of the enzyme that non-specifically degrades 2-monoacylglycerol is not particularly limited, and may be, for example, a positional non-specific lipase derived from any one selected from the group consisting of yeast, fungi, and bacteria.

As used herein, the term "positional non-specific lipase" refers to a lipase that reacts with all three fatty acyl groups in triglycerides.

In another embodiment of the present invention, as the positional non-specific lipase, a *Candida rugosa*-derived lipase was used. However, in addition to the *Candida rugosa*-derived lipase, other non-specific lipases derived from microorganisms such as yeast, fungi, and bacteria can be used.

FIG. 8 illustrates results obtained by administering the *Candida rugosa*-derived lipase into 6-week-old mice for a total of 6 weeks and measuring changes in body weight. The 2-position-specific lipase specifically acts on only 2-monoacylglycerol, and thus exhibits further excellent substrate specificity and degradation activity as compared with the positional non-specific lipase, such that obesity can be treated in a more effective manner. Therefore, the 2-position specific lipase exhibits a superior therapeutic effect on obesity even in a case of being used alone without being combined with other additional ingredients.

Figure 10:
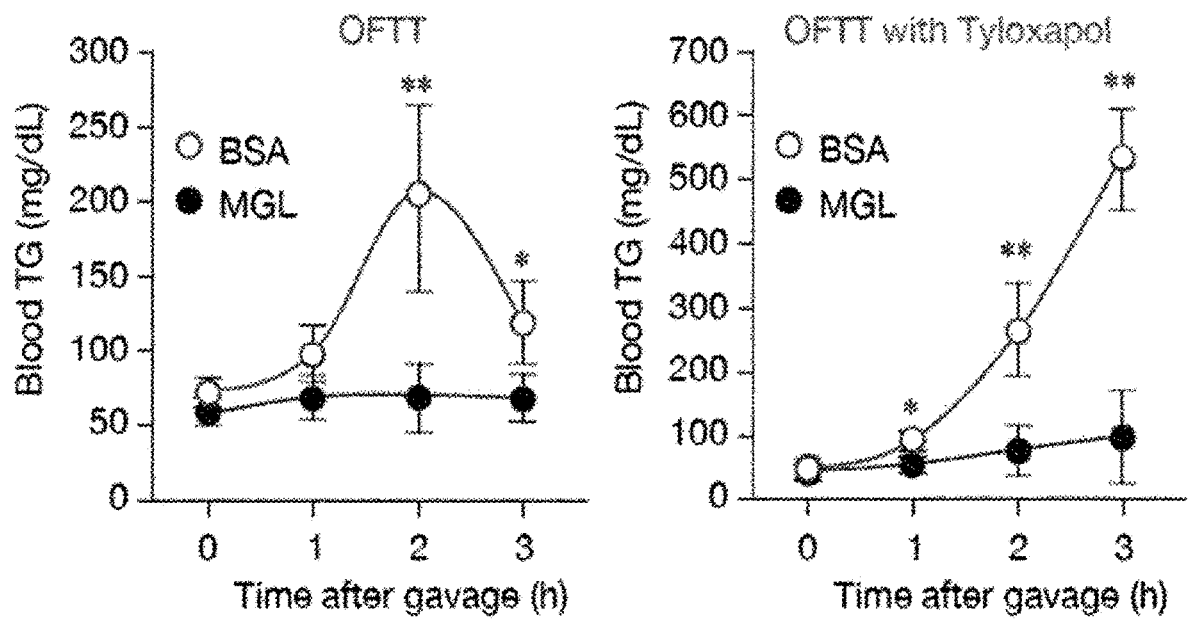
FIG. 10 illustrates graphs obtained by measuring, on an hourly basis, changes in blood triglyceride concentration caused by a monoacylglycerol lipase in mice into which olive oil has been administered, and the graphs indicate the presence or absence of tyloxapol administration.

FIG. 9 is data, illustrating changes in blood triglyceride concentration caused by a monoacylglycerol lipase (MGL) in mice into which olive oil has been administered. FIG. 10 illustrates graphs obtained by measuring, on an hourly basis, changes in blood triglyceride concentration caused by a monoacylglycerol lipase in mice into which olive oil has been administered. From these results, it was identified that administration of the monoacylglycerol lipase is effective in decreasing blood triglyceride, and these results show that the monoacylglycerol lipase can be used as a therapeutic agent for hyperlipemia.

Figure 11:
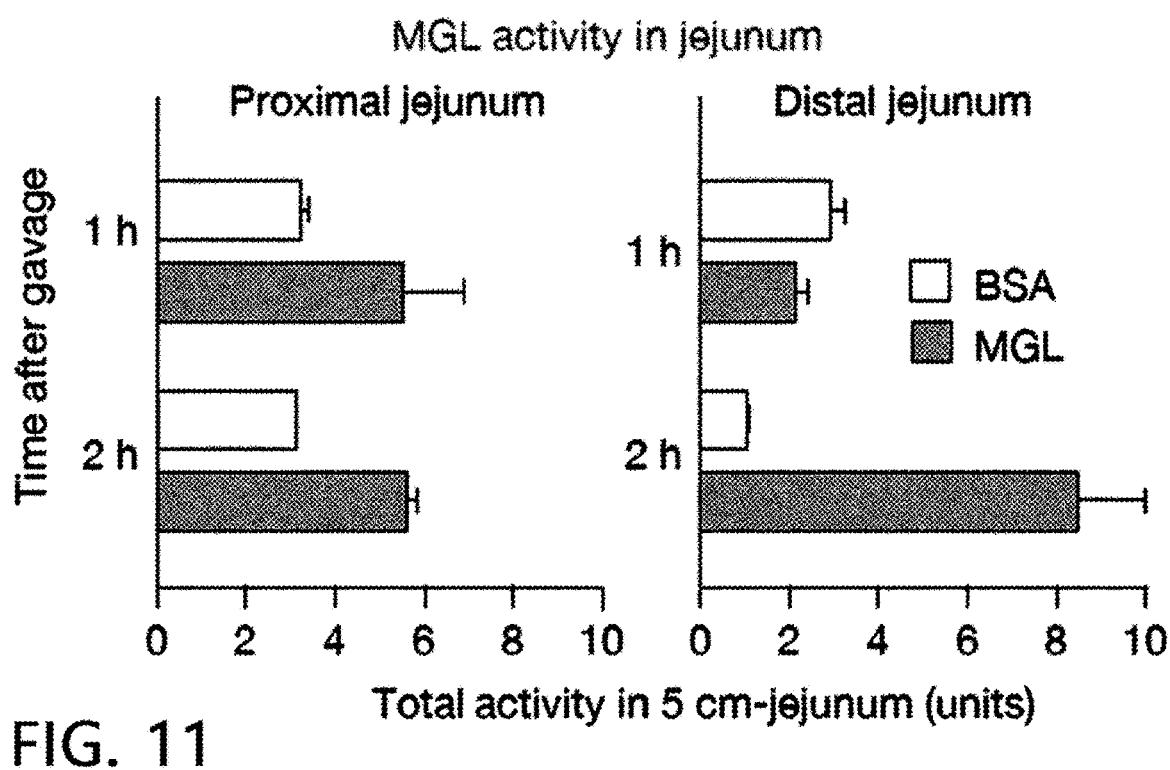
FIG. 11 illustrates results obtained by measuring activity of a monoacylglycerol lipase which acts in the small intestine at sacrifice of mice 1 hour and 2 hours after administration of the enzyme.
Figure 12:
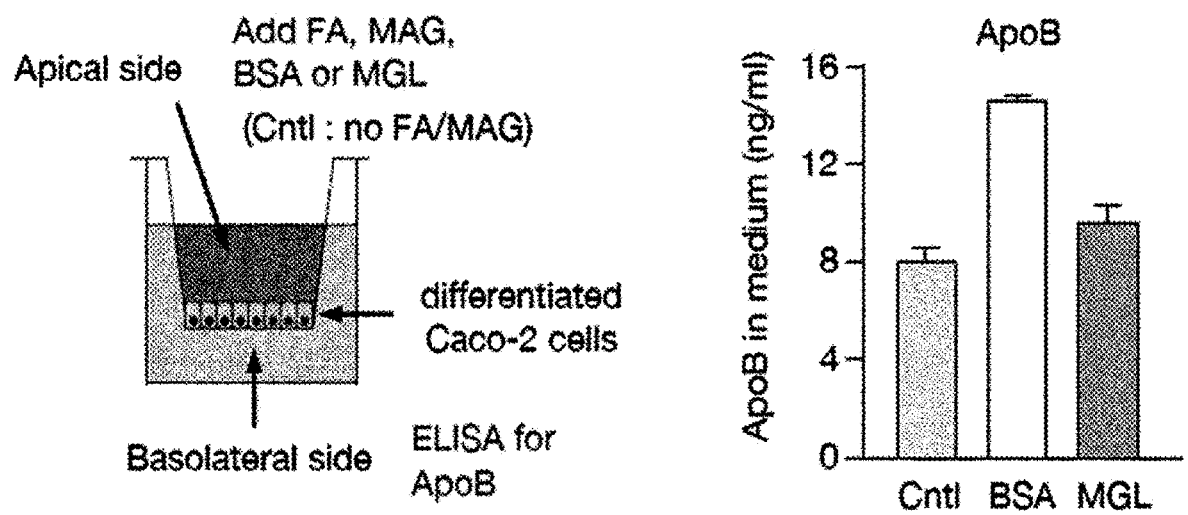
FIG. 12 illustrates results obtained by using Caco-2 cells which are a human small intestine epithelial cell line, and the results show that an ability of small intestine epithelial cells to perform fat recombination is decreased due to administration of a monoacylglycerol lipase.

FIGS. 11 and 12 illustrate results which show, respectively, that a monoacylglycerol lipase acts in the small intestine after administration, and that the monoacylglycerol lipase exhibits an effect of delaying fat recombination in Caco-2 cells which are a human small intestine epithelial cell line.

Figure 13A:
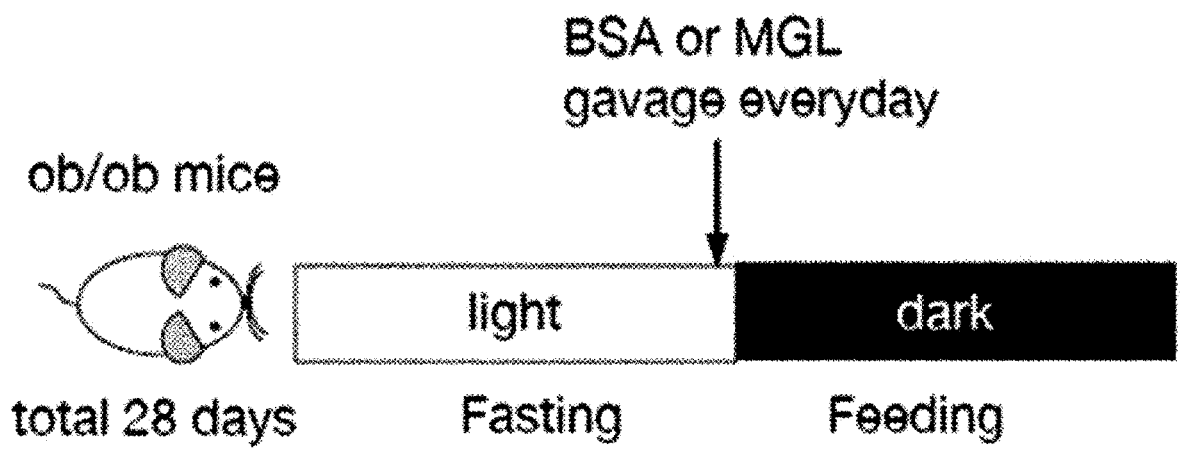
FIG. 13A is a schematic diagram, illustrating a sample administration schedule in an experiment in which obesity-induced ob/ob mice have been administered BSA or a monoacylglycerol lipase (MGL) for 4 weeks.
Figure 13B:
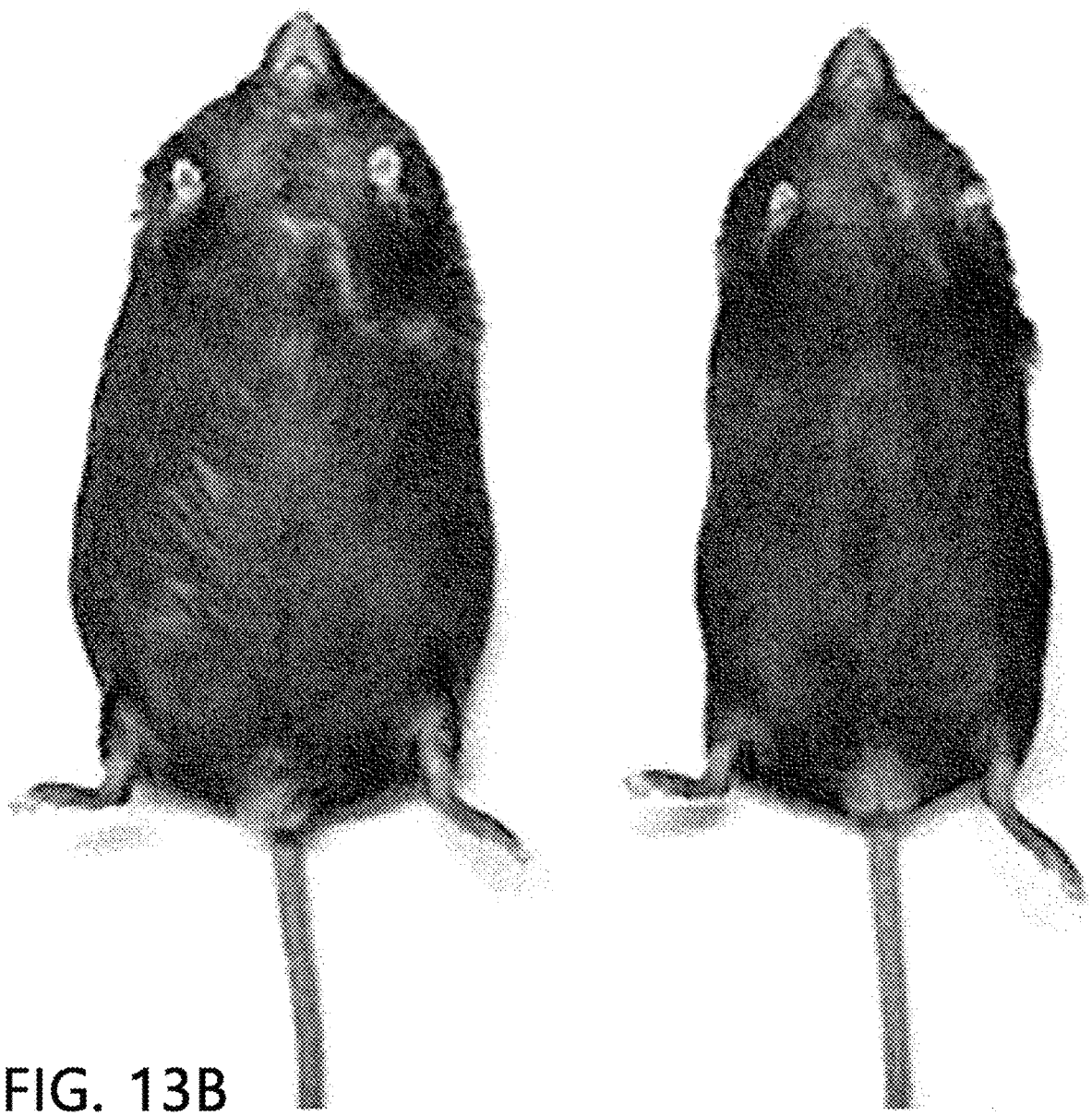
FIG. 13B is a photograph, illustrating appearances of mice of the BSA-administered group and the MGL-administered group after the end of the experiment of FIG. 13A.
Figure 13D:
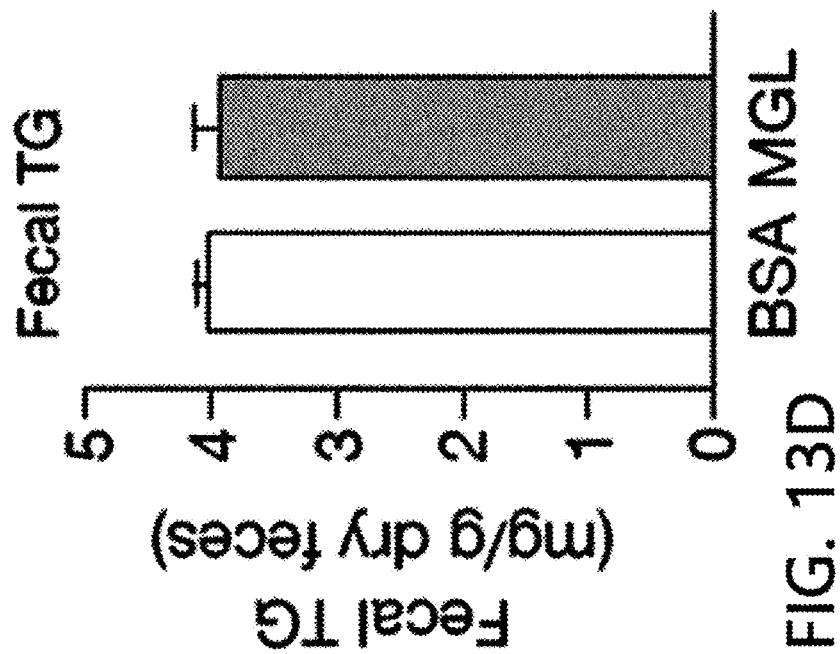
FIG. 13D illustrates fecal fat levels in the BSA-administered group and the MGL-administered group in the experiment of FIG. 13A.
Figure 13C:
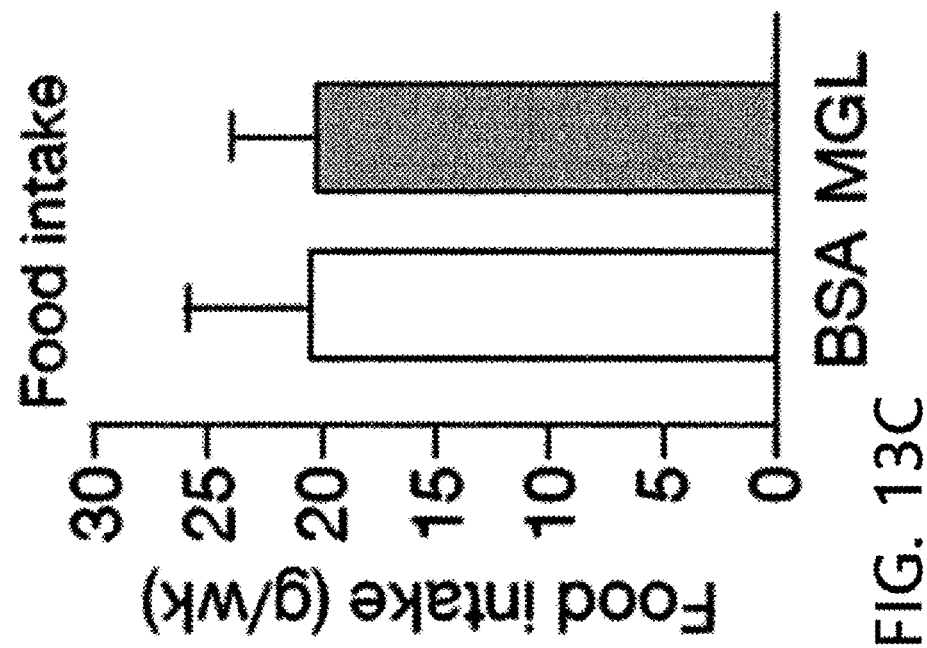
FIG. 13C illustrates dietary amounts in the BSA-administered group and the MGL-administered group in the experiment of FIG. 13A.
Figure 13E:
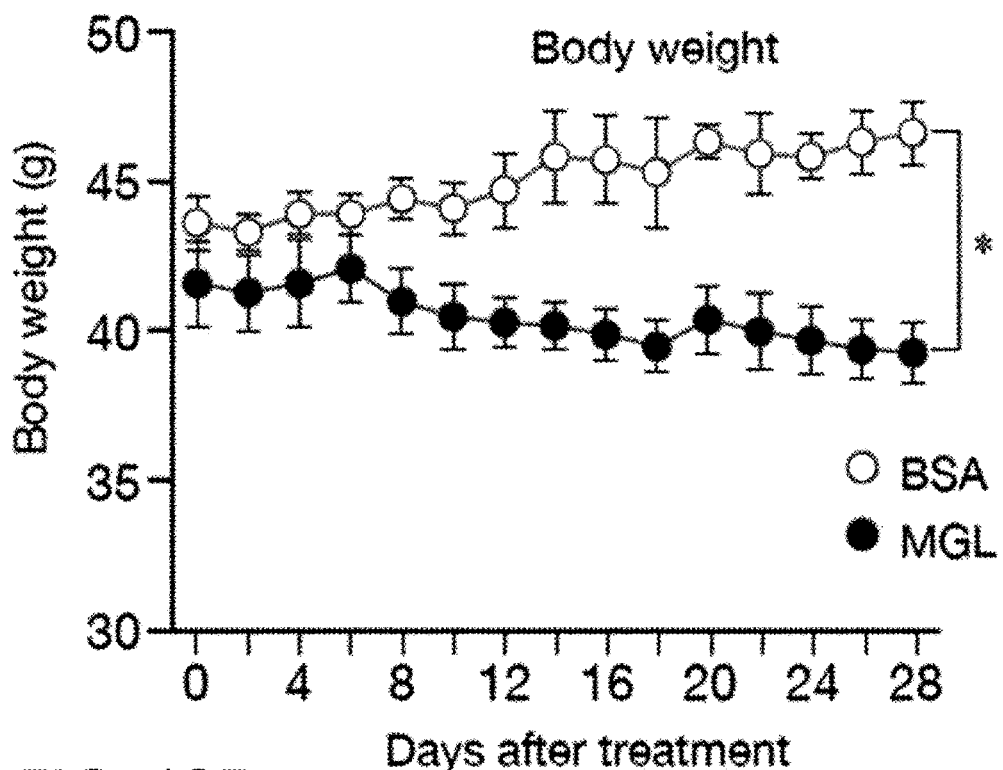
FIG. 13E graphically illustrates changes in body weight in the BSA-administered group and the MGL-administered group during the experiment of FIG. 13A.
Figure 13F:
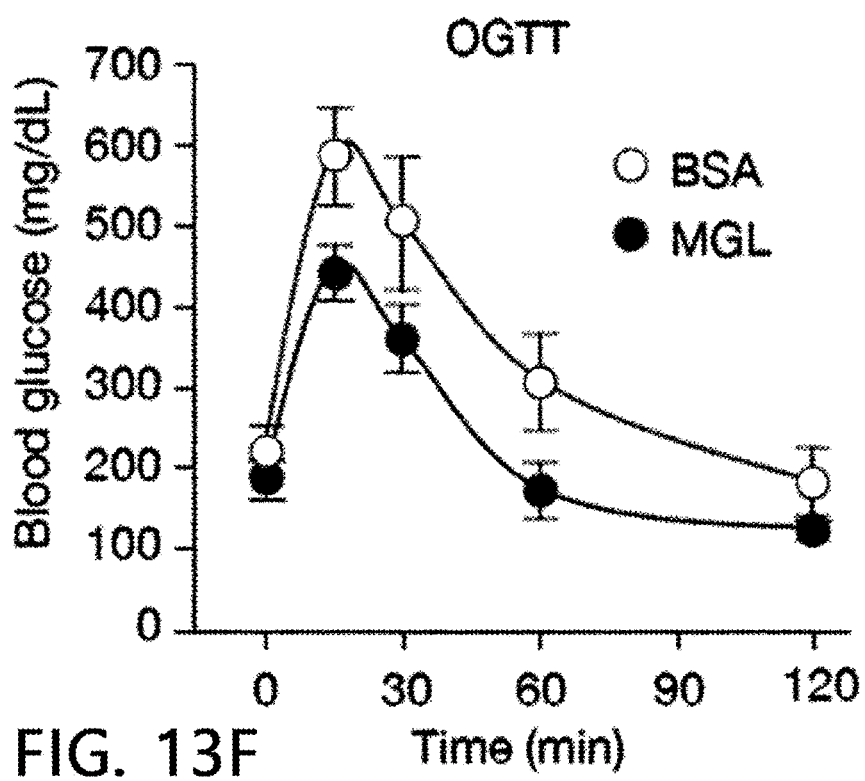
FIG. 13F graphically illustrates results obtained by performing a glucose loading test for the mice of the BSA-administered group and the MGL-administered group after the end of the experiment of FIG. 13A.
Figure 13G:
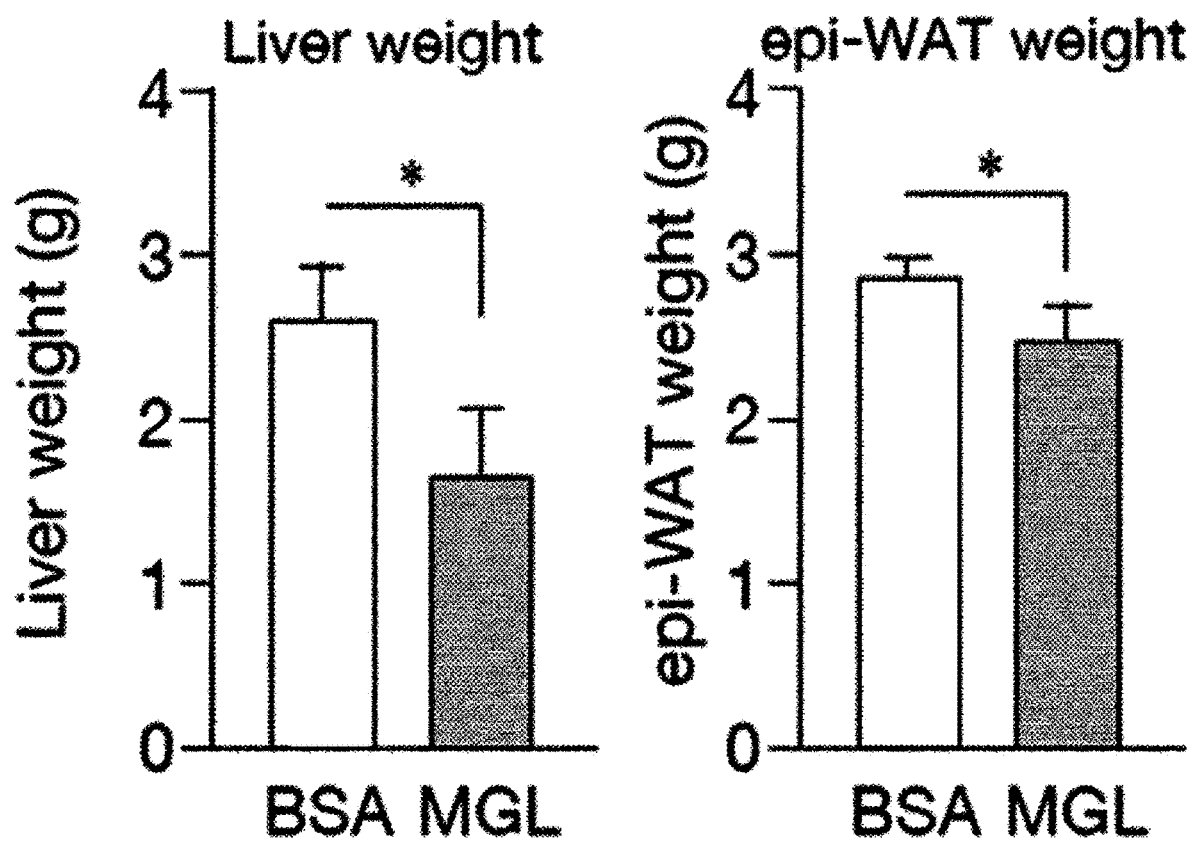
FIG. 13G graphically illustrates results obtained by measuring weights of liver and epididymal fat (Epi-WAT) in the mice of the BSA-administered group and the MGL-administered group after the end of the experiment of FIG. 13A.

FIGS. 13A to 13G illustrate results obtained by administering a monoacylglycerol lipase (MGL) into obesity-induced ob/ob mice for 4 weeks and then measuring changes in body weight (FIGS. 13B and 13E), changes in dietary amount (FIG. 13C), fecal fat levels (FIG. 13D), glucose loading test results (FIG. 13F), and weights of liver and epididymal fat (Epi-WAT) (FIG. 13G). In addition, FIGS. 14A to 14D are extensions of the experiment of FIG. 13A, illustrating appearances of livers (FIG. 14A) after obesity-induced ob/ob mice were administered the monoacylglycerol lipase (MGL) for 4 weeks, triglyceride and cholesterol levels in the livers (FIG. 14B), appearances of epididymal fat tissue (FIG. 14C), and an average size of adipocytes in the fat tissue (FIG. 14D).

From the above experimental results, it was possible to identify a decrease in body weight, a decrease in fatty liver as seen in a liver size, and a decrease in epididymal fat which are caused by administration of MGL. Therefore, it can be seen that long-term administration of the monoacylglycerol lipase is effective in alleviating liver steatosis or non-alcoholic fatty liver and decreasing a body weight, which suggests that the monoacylglycerol lipase can be utilized as a therapeutic agent for liver steatosis or non-alcoholic fatty liver, and a therapeutic agent for obesity.

In addition, it was identified that administration of the monoacylglycerol lipase does not cause changes in dietary amount and exhibits no side effects such as fatty stool. The fatty stool is a severe side effect of Xenical which is one of conventional therapeutic agents for obesity. The monoacylglycerol lipase of the present invention exhibits an effect of decreasing a total body weight by 15% without exhibiting such a side effect. Thus, it was identified that the monoacylglycerol lipase of the present invention exerts superior efficacy as a therapeutic agent for obesity.

Upon making a direct comparison between results of FIGS. 8 and 13E, FIG. 8 illustrates a body weight-decreasing effect after administering a *Candida rugosa*-derived lipase, which is a type of positional non-specific lipase, in an amount of 2,000 units/day, and FIG. 13E illustrates a body weight-decreasing effect after administering the monoacylglycerol lipase, which is a 2-position specific lipase, in an amount of about 100 units/day. In both of the above examples, an effect of decreasing a body weight by about 3 g was similarly exhibited. This indicates that (1) activity per protein of the 2-position specific lipase is much higher than that of the positional non-specific lipase (50 to 100 times) in a reaction where monoacylglycerol is used as a substrate, indicates that (2) affinity of the positional non-specific lipase for 2-monoacylglycerol is not as good as the 2-position specific lipase, and suggests that (3) the 2-position specific lipase does not affect degradation of triglyceride by physiological digestive fluids and does not cause a phenomenon that triglyceride, which does not need to be absorbed, is rather degraded. This fact implies that the 2-position specific lipase can exhibit a much better therapeutic effect than the positional non-specific lipase.

In addition, obesity-induced ob/ob mice were administered the monoacylglycerol lipase of the present invention for 4 weeks, and then a glucose loading test was performed. As a result, obesity was alleviated due to administration of the monoacylglycerol lipase. Therefore, as illustrated in FIG. 13F, it was identified that metabolism in a body is improved, and thus an ability to process glucose is enhanced. These results show that administration of the monoacylglycerol lipase of the present invention can be linked to treatment of metabolic syndrome such as type 2 diabetes.

Figure 15A:
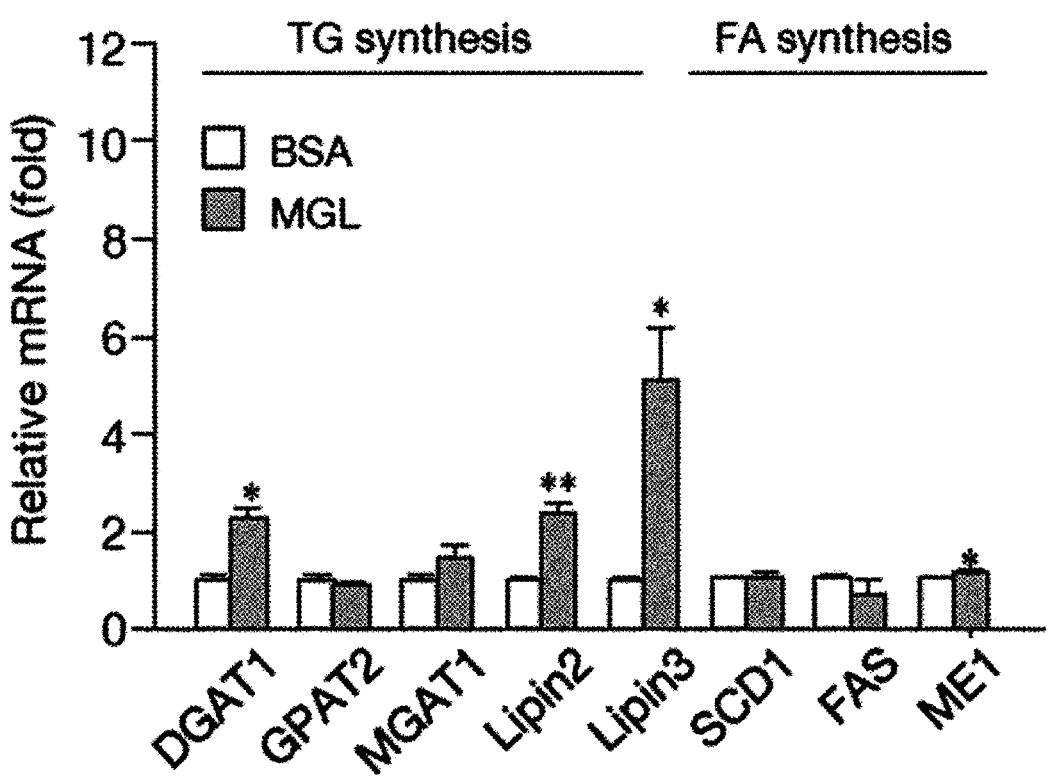
FIG. 15A graphically illustrates changes in expression of genes for triglyceride synthesis and genes for fatty acid synthesis in inguinal fat of the mice of the BSA-administered group and the MGL-administered group after the end of the experiment of FIG. 13A.
Figure 15B:
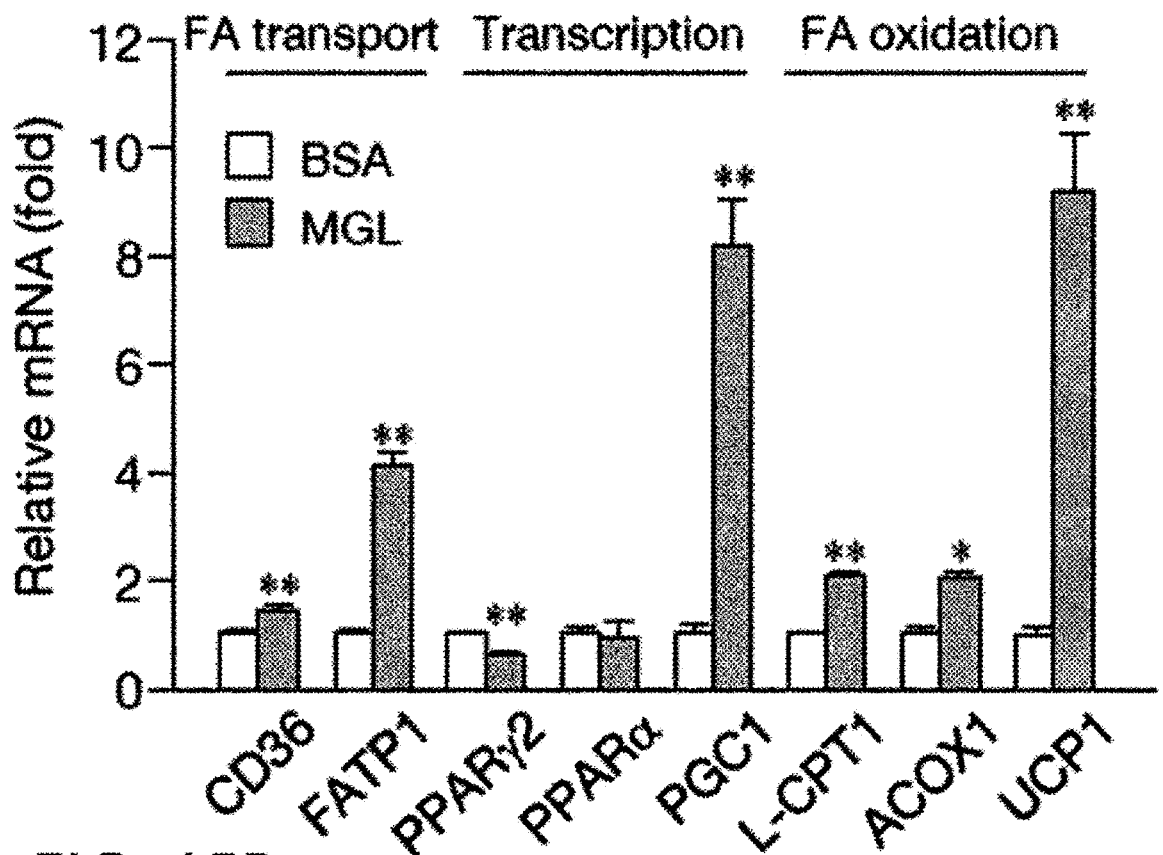
FIG. 15B graphically illustrates changes in expression of genes for fatty acid transport, genes for fatty acid transcription, and genes for fatty acid oxidation in inguinal fat of the mice of the BSA-administered group and the MGL-administered group after the end of the experiment of FIG. 13A.

FIGS. 15A and 15B are also extensions of the experiment of FIG. 13A. FIG. 15A illustrates changes in expression of genes for triglyceride synthesis and genes for fatty acid synthesis in inguinal fat, which can be considered subcutaneous fat tissue, of the mice of the BSA-administered group and the MGL-administered group. FIG. 15B illustrates changes in expression of genes for fatty acid transport, genes for fatty acid transcription, and genes for fatty acid oxidation in the inguinal fat. From these results, it can be seen that expression of the genes for triglyceride synthesis and the genes for fatty acid synthesis is not changed or is rather increased in the MGL-administered group, and that the genes for fatty acid transport also exhibit a similar pattern. These results mean that a decrease in fat accumulation in the MGL-administered group is due to decreased absorption or consumption in a digestive tract, and does not result from a decrease in triglyceride synthesis or transport or fatty acid synthesis. One unusual thing is that expression of PGC1 and UCP1 is remarkably increased in the MGL-administered group, which means that browning of white fat is occurring and energy consumption is increased.

Figure 16A:
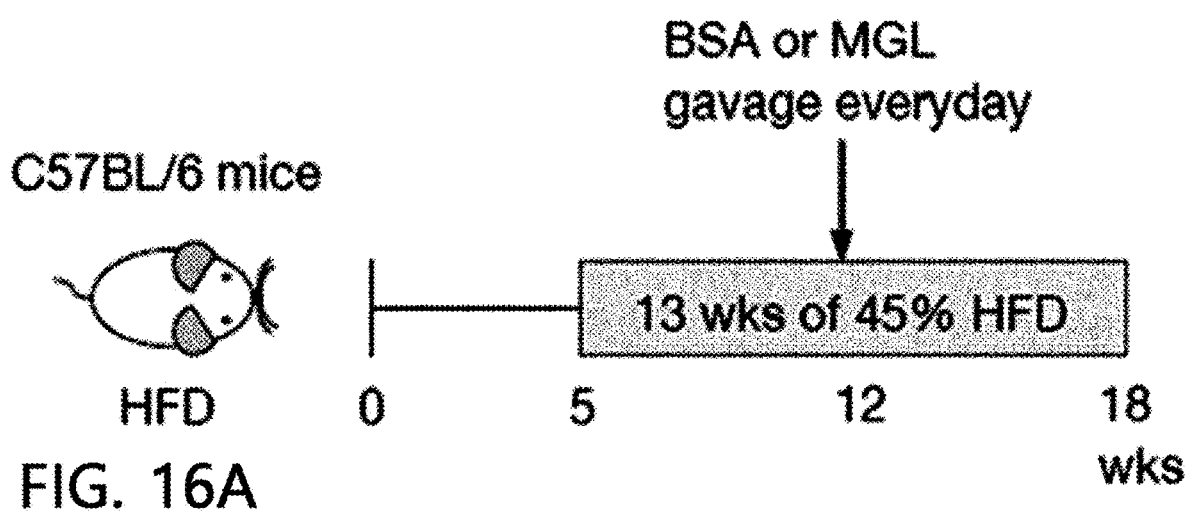
FIG. 16A is a schematic diagram, illustrating a sample administration schedule in an experiment in which C57BL/6 mice fed a high-fat diet have been administered BSA or MGL.
Figure 16B:
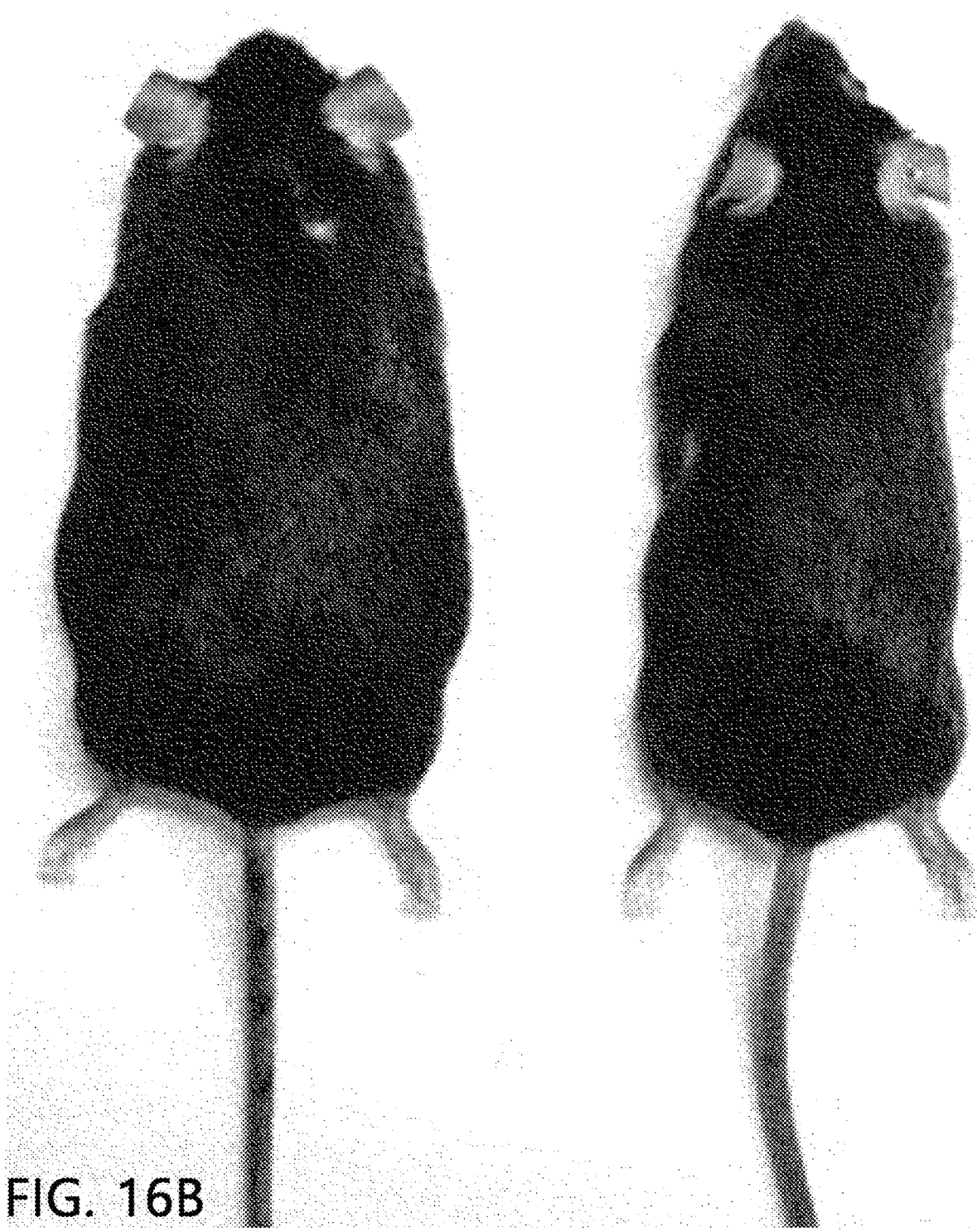
FIG. 16B is a photograph, illustrating the mice of the BSA-administered group and the MGL-administered group after the end of the experiment of FIG. 16A.
Figure 16D:
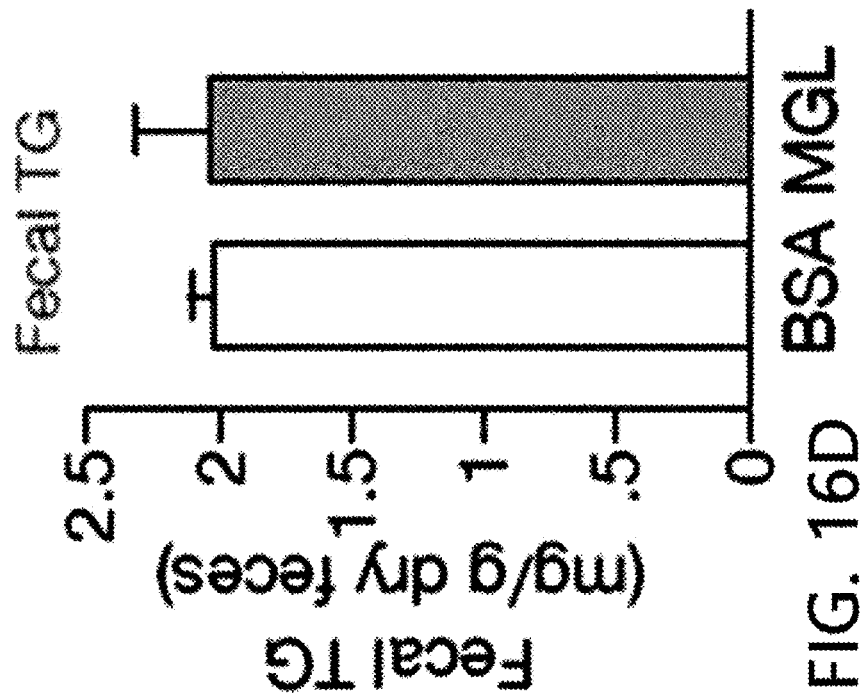
FIG. 16D illustrates fecal fat levels in the BSA-administered group and the MGL-administered group in the experiment of FIG. 16A.
Figure 16C:
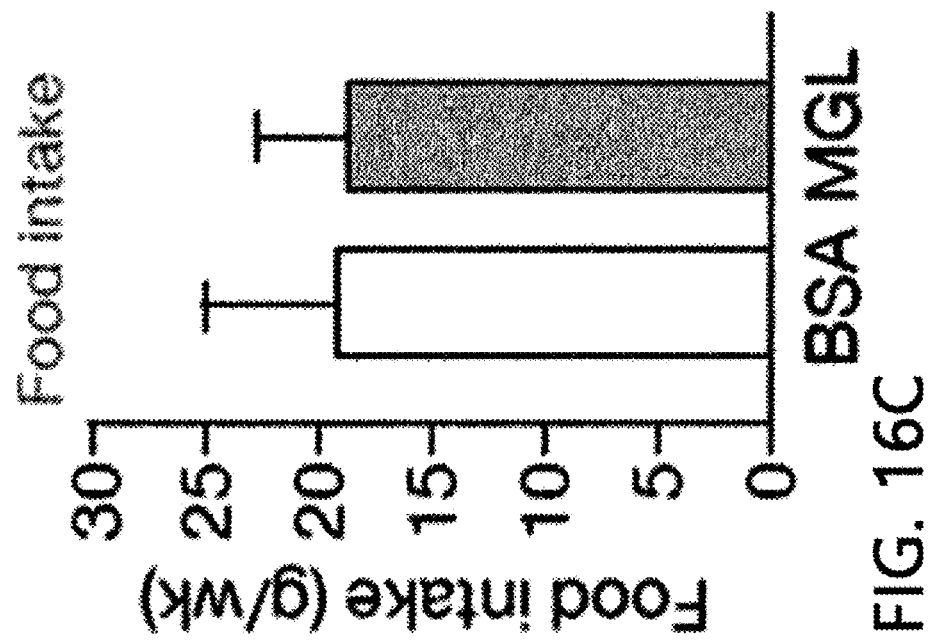
FIG. 16C illustrates dietary amounts in the BSA-administered group and the MGL-administered group in the experiment of FIG. 16A.
Figure 16E:
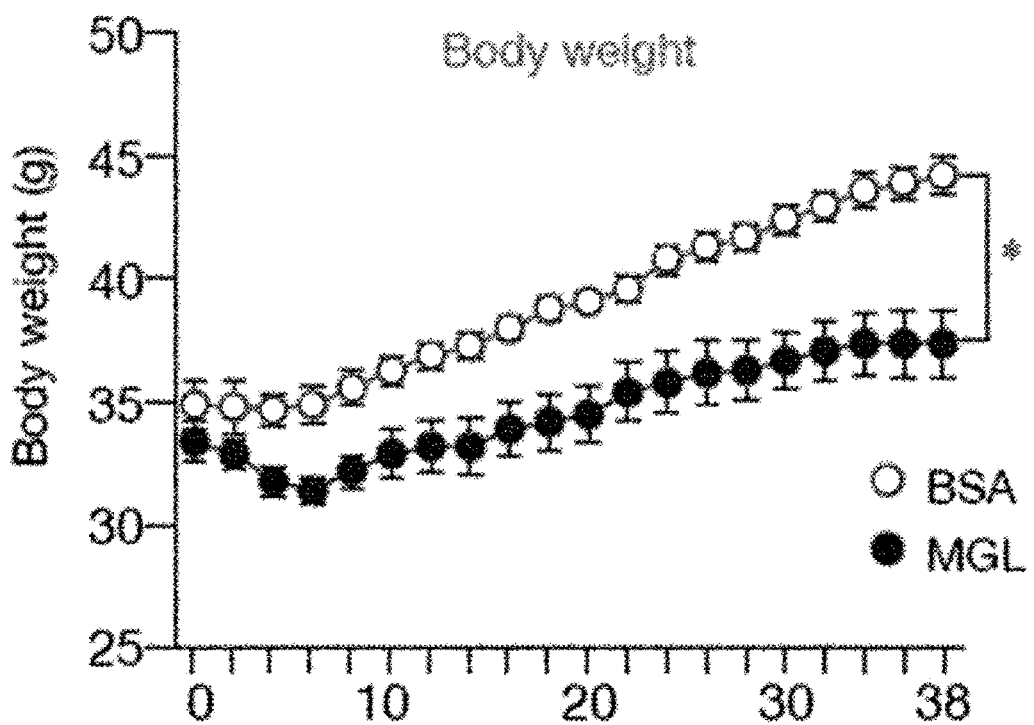
FIG. 16E graphically illustrates changes in body weight in the BSA-administered group and the MGL-administered group during the experiment of FIG. 16A.
Figure 16F:
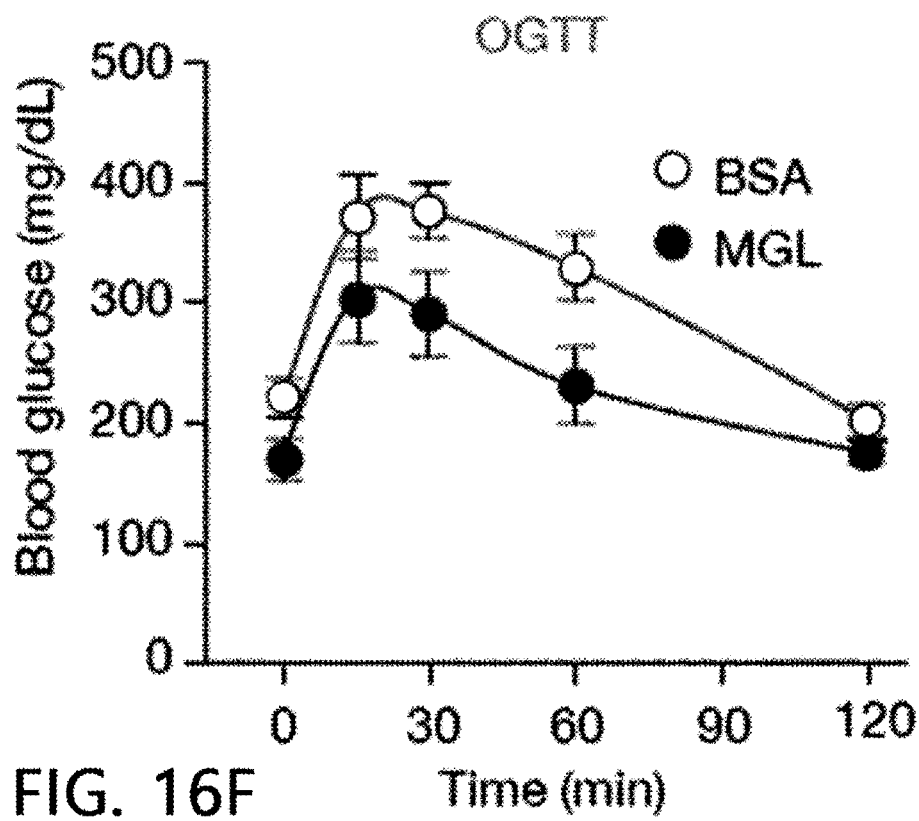
FIG. 16F graphically illustrates results obtained by performing a glucose loading test for the mice of the BSA-administered group and the MGL-administered group after the end of the experiment of FIG. 16A.
Figure 16G:
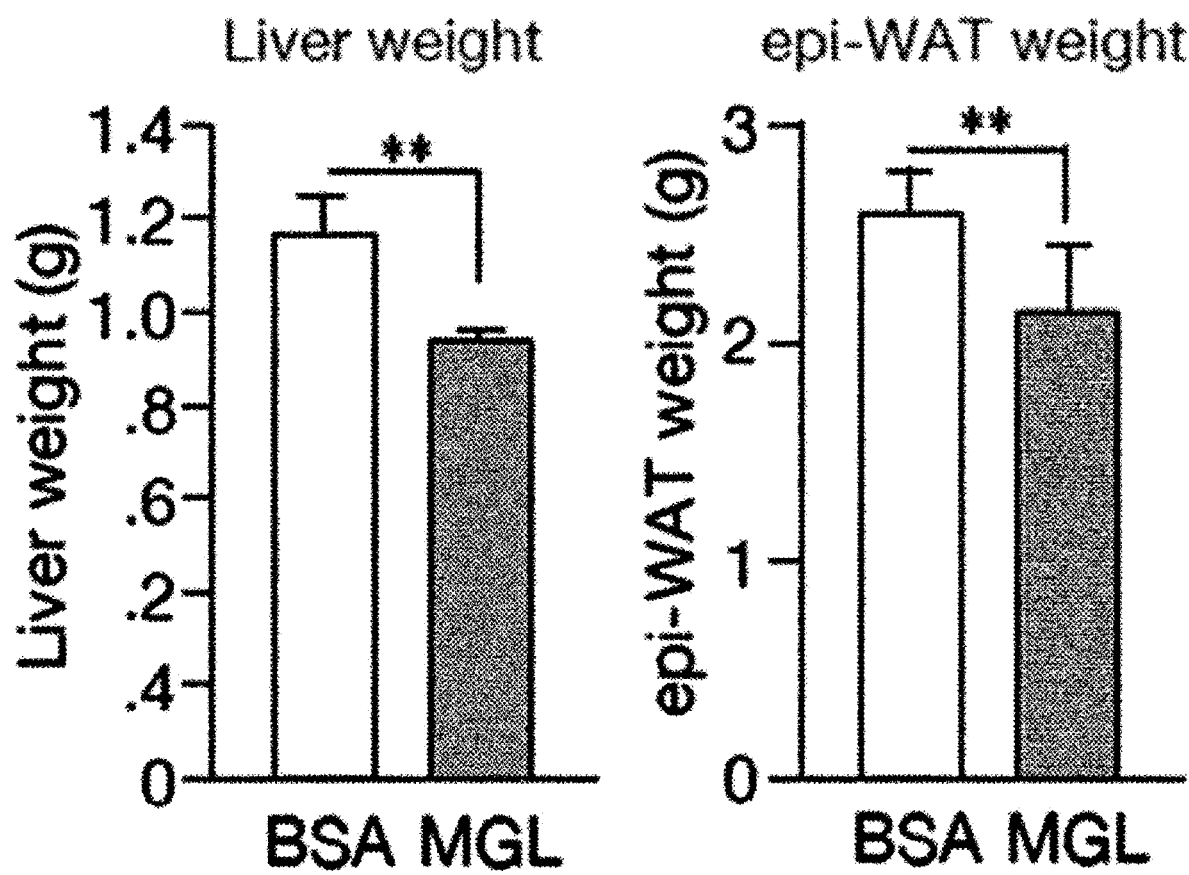
FIG. 16G graphically illustrates results obtained by measuring weights of liver and epididymal fat (Epi-WAT) in the mice of the BSA-administered group and the MGL-administered group after the end of the experiment of FIG. 16A.

FIGS. 16A to 16G illustrate results obtained by administering MGL into C57BL/6 mice fed a high-fat diet, and then measuring changes in body weight (FIGS. 16B and 16E), changes in dietary amount (FIG. 16C), fecal fat levels (FIG. 16D), glucose loading test results (FIG. 16F), and weights of liver and epididymal fat (Epi-WAT) (FIG. 16G). Similar to the results in obesity-induced ob/ob mice (FIGS. 13B to 13G), it was identified that administration of MGL exhibits an effect of decreasing a total body weight by about 15%, exhibits no changes in dietary amount, and exhibits no side effects such as fatty stool. In addition, it was identified that improved glucose tolerance is exhibited in the glucose loading test, and weights of liver and fat tissue are considerably decreased.

Figure 17A:
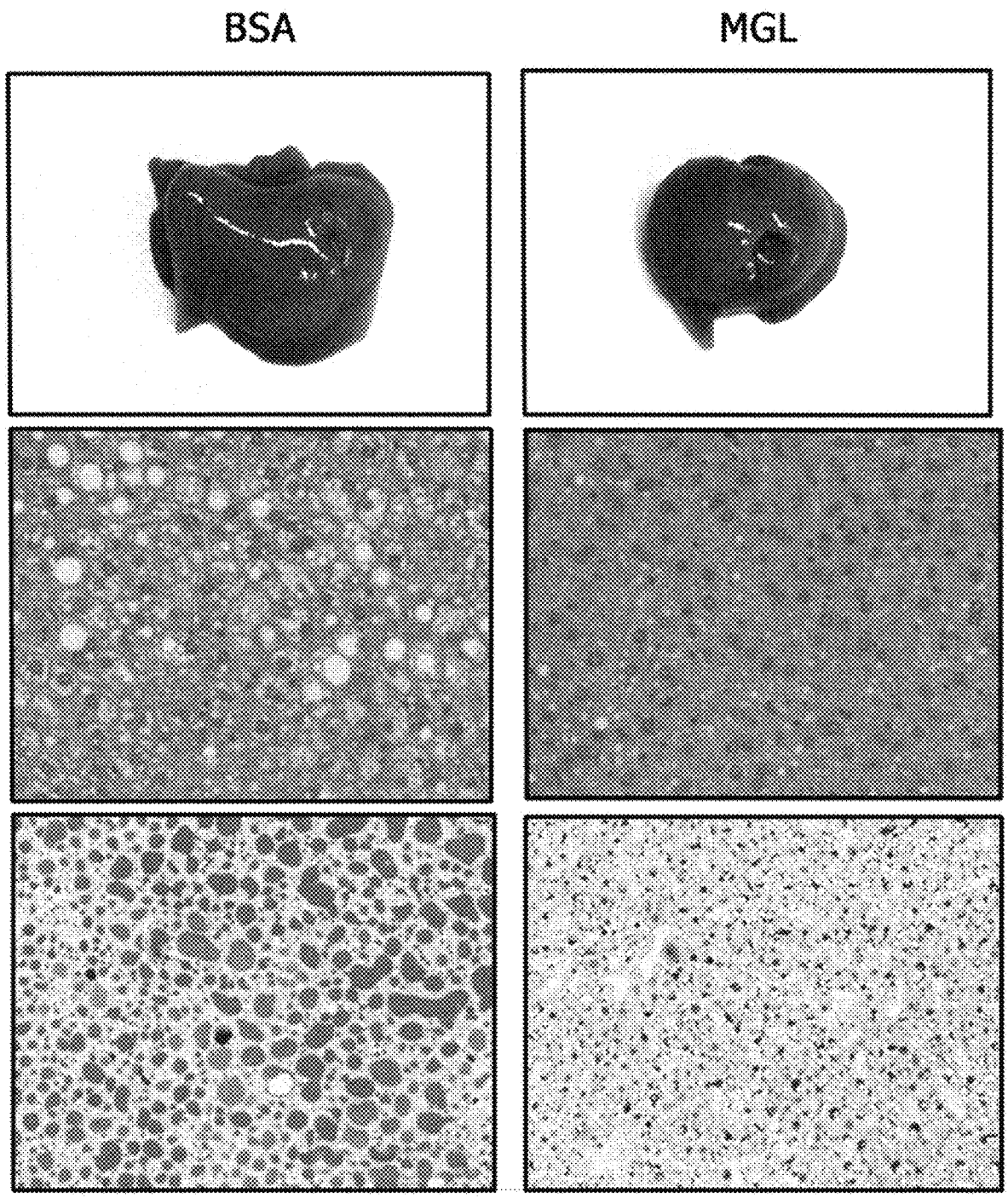
FIG. 17A illustrates appearances of livers (upper panels), which have been extracted from the mice of the BSA-administered group and the MGL-administered group after the end of the experiment of FIG. 16A, photographs (middle panels) obtained by staining the livers with H&E and making an observation using a tissue microscope, and photographs (lower panels) obtained by staining the livers with oil-red O and making an observation using a tissue microscope.
Figure 17B:
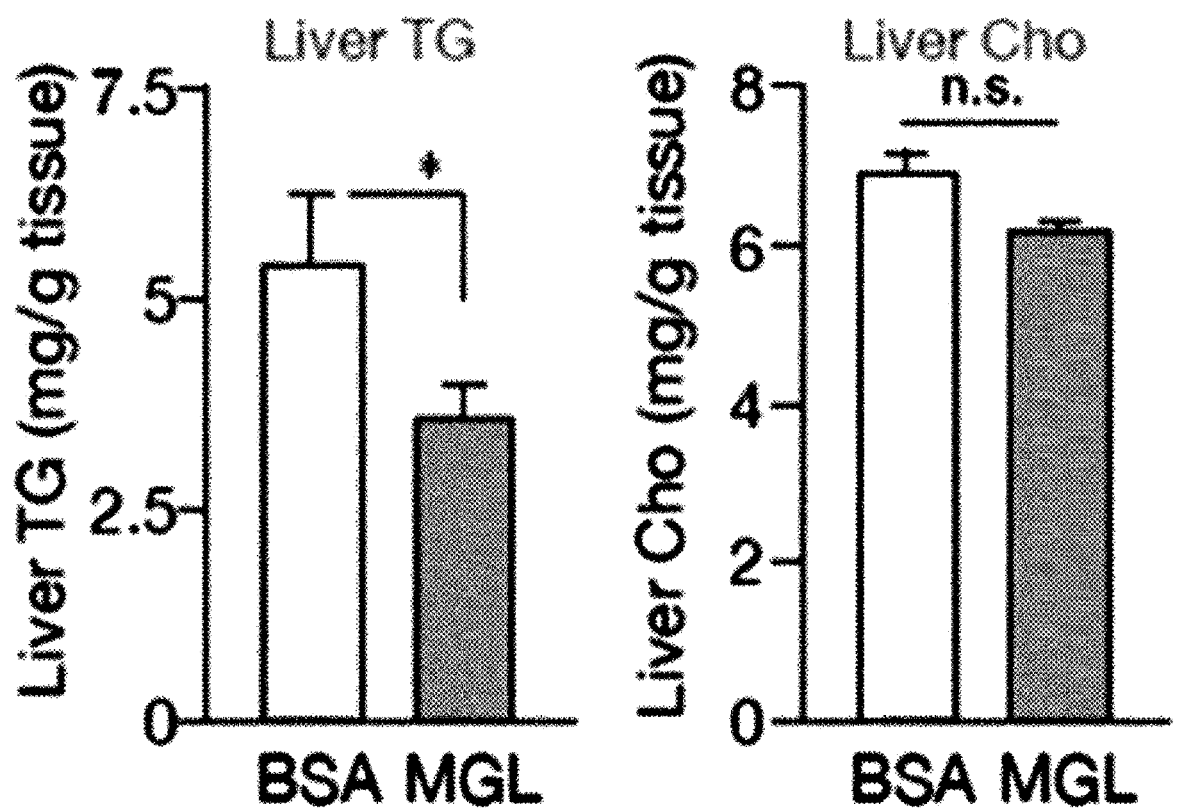
FIG. 17B graphically illustrates results obtained by measuring triglyceride and cholesterol levels in the livers of FIG. 17A.
Figure 17C:
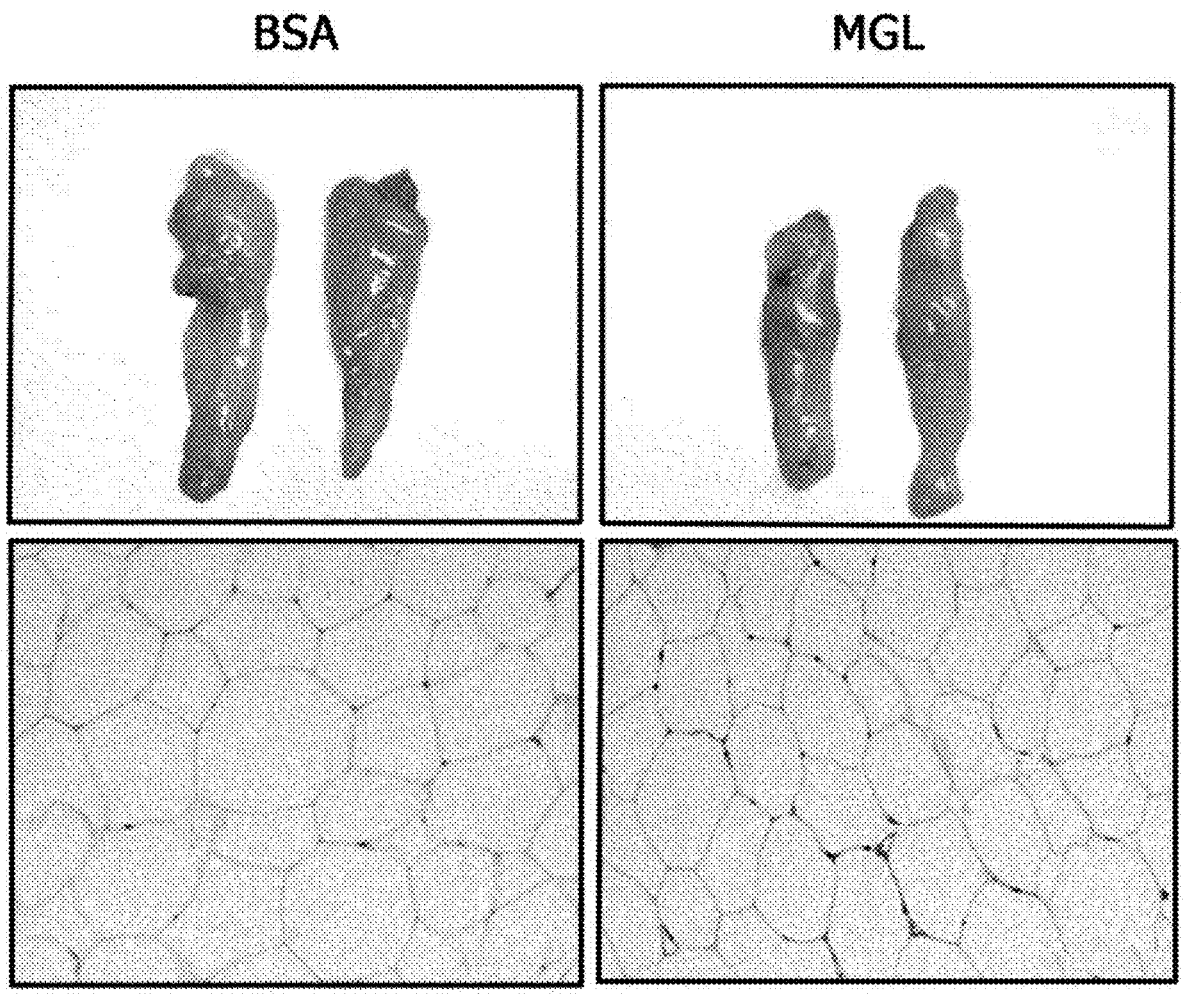
FIG. 17C illustrates appearances of epididymal fat tissue (upper panels), which has been extracted from the mice of the BSA-administered group and the MGL-administered group after the end of the experiment of FIG. 16A, and photographs (lower panels) obtained by observing the fat tissue using a tissue microscope.
Figure 17D:
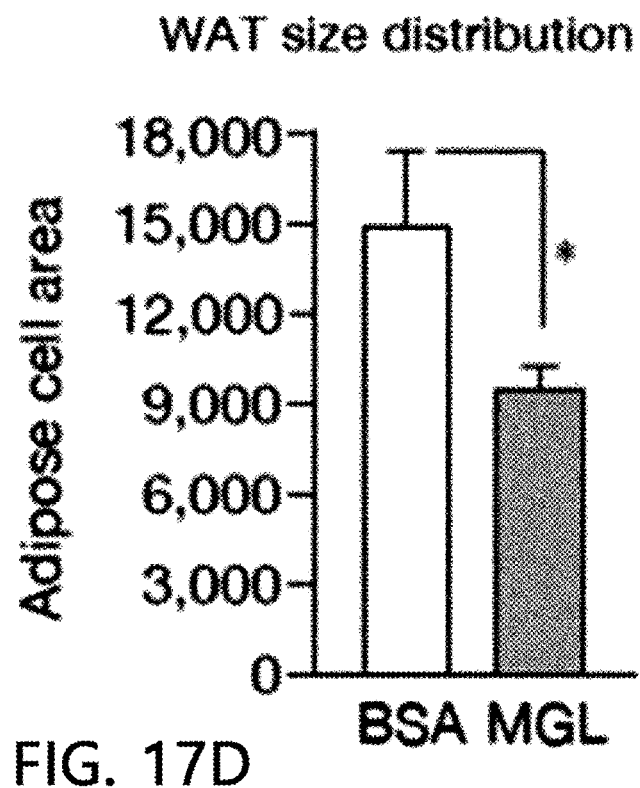
FIG. 17D graphically illustrates results obtained by measuring an average size of adipocytes in the fat tissue of FIG. 17C.
Figure 17E:
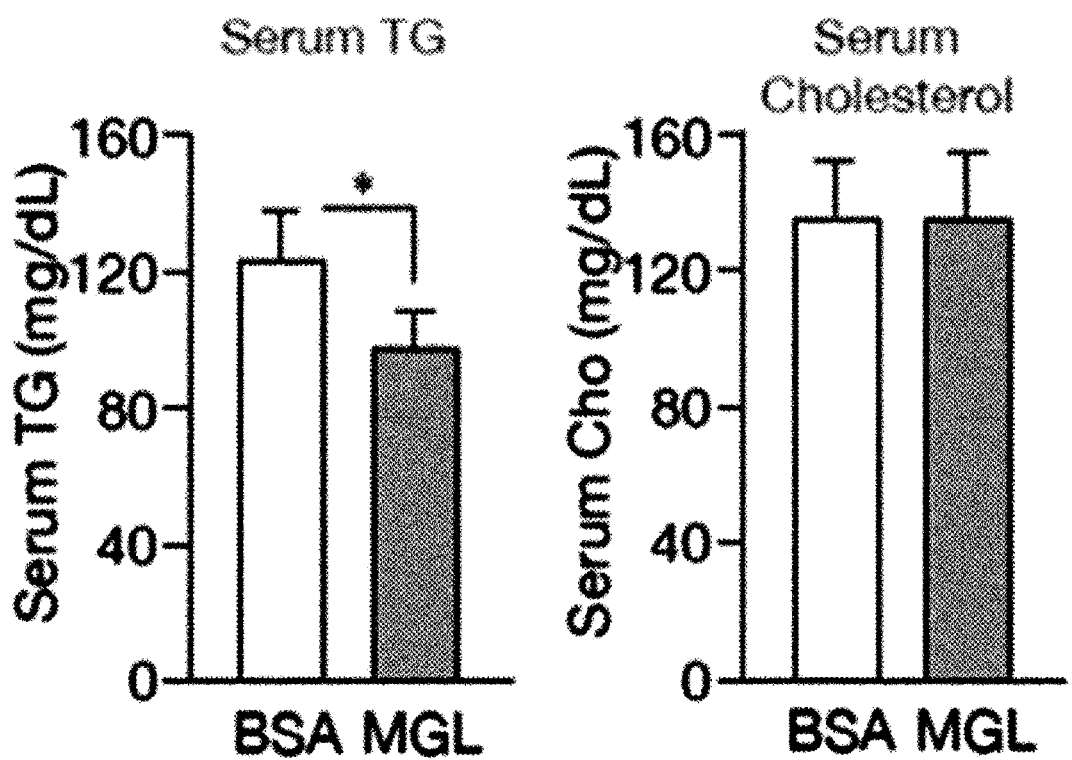
FIG. 17E graphically illustrates results obtained by measuring blood triglyceride and blood cholesterol levels in the mice of the BSA administration group and the MGL administration group after the end of the experiment of FIG. 16A.
Figure 17F:
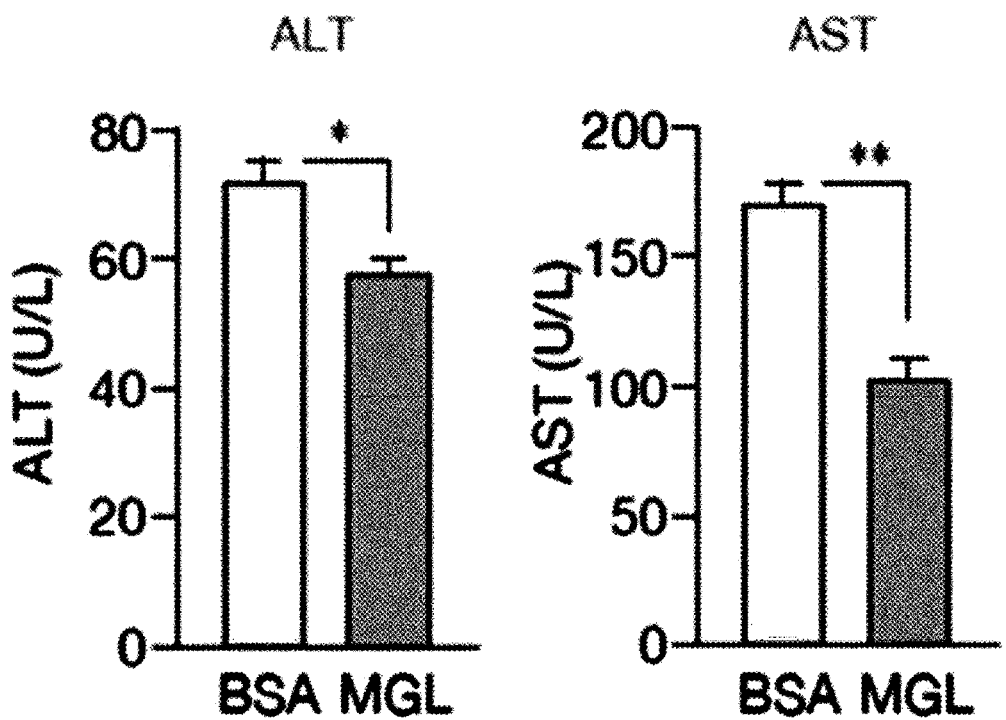
FIG. 17F graphically illustrates results obtained by measuring ALT and AST, which are numerical values for liver, in the mice of the BSA administration group and the MGL administration group after the end of the experiment of FIG. 16A.
Figure 17G:
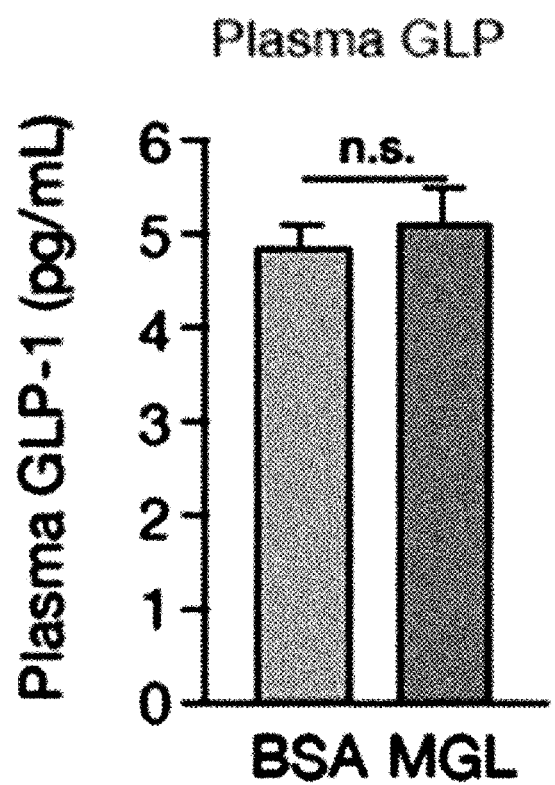
FIG. 17G graphically illustrates results obtained by measuring blood GLP-1 levels in the mice of the BSA administration group and the MGL administration group after the end of the experiment of FIG. 16A.

FIGS. 17A to 17G are extensions of the experiment of FIG. 16A, and illustrate results obtained by administering MGL into C57BL/6 mice fed a high-fat diet, and then measuring appearances of livers (FIG. 17A), triglyceride and cholesterol levels in the livers (FIG. 17B), appearances of epididymal fat tissue (FIG. 17C) and an average size of adipocytes in the fat tissue (FIG. 17D), blood triglyceride and cholesterol levels (FIG. 17E), ALT and AST, which are numerical values for liver (FIG. 17F), and changes in blood GLP(FIG. 17G). From these results, it can be seen that the MGL-administered group exhibits remarkably improved fatty liver, a greatly decreased liver triglyceride level, and a decreased cholesterol level, as compared with the BSA-administered group. In addition, it was possible to identify that sizes of fat tissue and adipocytes are decreased, an average size of adipocytes is decreased, and blood triglyceride is decreased. A numerical value for liver such as ALT and AST was considerably decreased, and there was no change in GLP-1 which is known to be able to affect diet.

Figure 18:
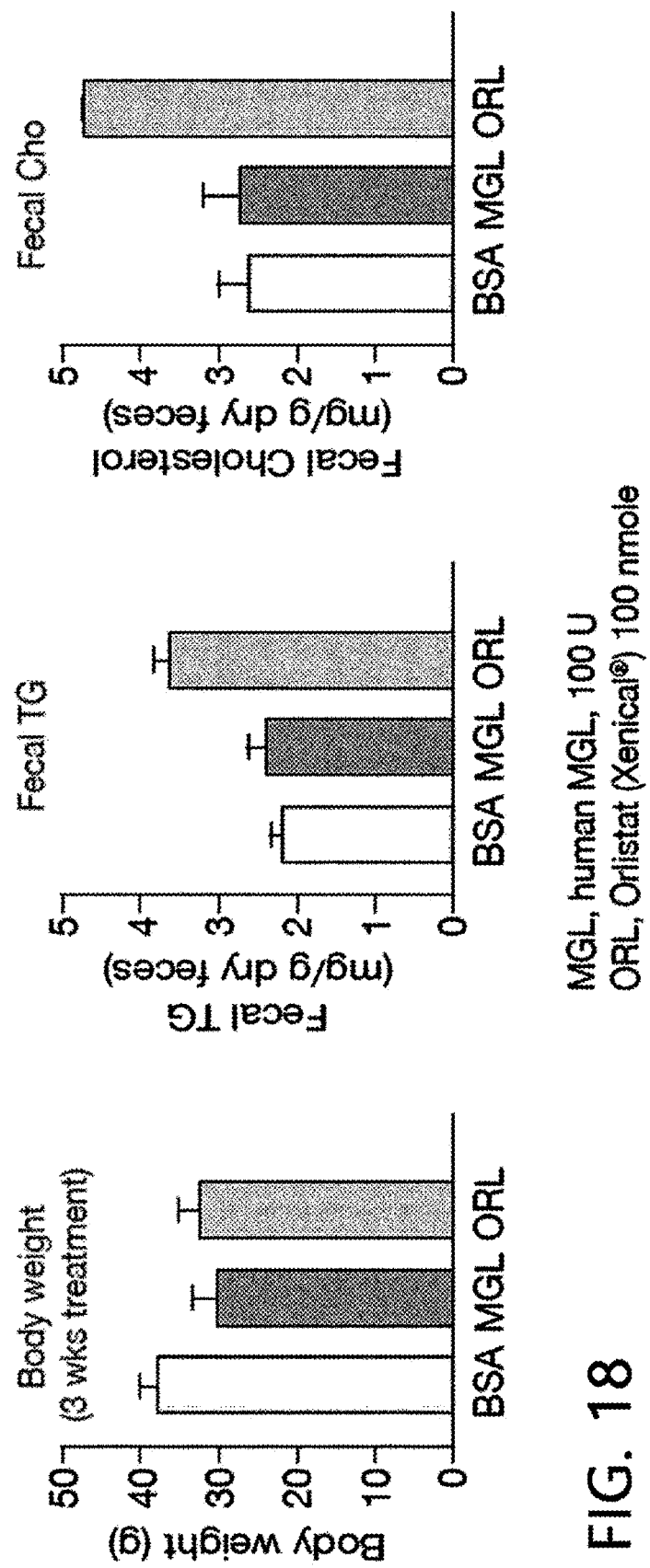
FIG. 18 graphically illustrates results obtained by measuring body weights, fecal fat levels, and fecal cholesterol levels after administering MGL of the present invention or Xenical (orlistat, ORL) into C57BL/6 mice for 3 weeks.
Figure 19:
FIG. 19 illustrates a photograph of gallbladder lesion found in mice that died in the Xenical-administered group during the experiment of FIG. 18.

FIG. 18 illustrates results obtained by performing a comparative experiment using the MGL-administered group of the present invention and Xenical (ORL)-administered group, in which Xenical is known as a conventional therapeutic agent for obesity. A similar degree of body weight-decreasing effect was observed in the MGL-administered group and the ORL-administered group. However, it was identified that a fecal fat level and a cholesterol level were remarkably high in the ORL-administered group. Additionally, autopsy was performed on four mice that died during the experiment in the ORL-administered group. As a result, as illustrated in FIG. 19, a finding that gallbladder had turned black was obtained, which is determined to be pigmented gall stone among symptoms reported as side effects of Xenical.

From the above results, it was possible to identify that administration of MGL of the present invention exhibits a superior anti-obesity effect and a therapeutic effect on fatty liver. In particular, MGL of the present invention exhibits a body weight-decreasing effect which corresponds to a 15% body weight decrease in a total body weight in a case of being administered for 4 weeks. An anti-obesity agent which has been developed and is currently used is considered to be a good drug in a case where the anti-obesity agent exhibits an 8% to 11% body weight-decreasing effect when administered for 1 year. In consideration of this, it is determined that the result which has been demonstrated in the mouse experiment of the present invention is nearly the maximum effect and exhibits a very excellent body weight-decreasing effect. Additionally, in a case where a comparison is made in terms of effects with Xenical which is currently used as a therapeutic agent for obesity, due to the fact that MGL and Xenical are drugs having different properties and optimal doses thereof cannot be defined, it is not possible to determine a comparative advantage for a body-weight decreasing effect. However, MGL of the present invention exhibits no fatty stool and gallbladder lesion which are fatal disadvantages of Xenical, suggesting that MGL is an excellent drug which can substitute for a conventional therapeutic agent for obesity.

The pharmaceutical composition according to the present invention for prevention or treatment of liver steatosis, non-alcoholic fatty liver, hyperlipidemia, type 2 diabetes, and/or obesity, comprising a 2-monoacylglycerol degrading enzyme can be administered orally to a mammal such as a rat, a mouse, a domesticated animal, and a human. In addition, the pharmaceutical composition according to the present invention can be made into various formulations. In a case of being made into formulations, the formulations can be made using diluents or excipients such as fillers, extenders, binders, wetting agents, disintegrating agents, and surfactants which are commonly used in a range which does not inhibit activity of the 2-monoacylglycerol degrading enzyme. Solid formulations for oral administration include tablets, pills, powders, granules, capsules, and the like, and such solid formulations can be prepared by mixing the monoacylglycerol lipase with at least one excipient (for example, starch, sucrose, lactose, and gelatin) and the like. Preferably, a coating agent may be used to prevent activity of the 2-monoacylglycerol degrading enzyme from being destroyed by gastric acid and gastric juice. In addition to simple excipients, lubricants can also be used. Liquid formulations for oral administration can include suspensions, solutions, emulsions, syrups, and the like. The liquid formulations can contain various excipients, for example wetting agents, sweeteners, fragrances, and preservatives, in addition to water and liquid paraffin which are commonly used simple diluents. Formulations for parenteral administration can include sterile aqueous solutions, non-aqueous solvents, suspensions, emulsions, lyophilized preparations, and suppositories. For the non-aqueous solvents and suspensions, propylene glycol, polyethylene glycol, vegetable oil such as olive oil, injectable ester such as ethyl oleate, and the like can be used. As bases for the suppositories, glycerol, gelatin, and the like can be used.

A dosage of the pharmaceutical composition according to the present invention, comprising a 2-monoacylglycerol degrading enzyme may vary depending on a patient's age, sex, and body weight. However, for the pharmaceutical composition, in general, an amount of 1 to 500 unit/kg may be administered once a day or divided into several doses, in which 1 unit means an amount such that 1 mole of monoacylglycerol is completely degraded for 1 hour at a condition of pH 7.4 and 37° C. In addition, a dosage of the composition comprising a monoacylglycerol lipase can be increased or decreased depending on a route of administration, severity of disease, sex, body weight, age, and the like. Accordingly, the above dosage is not intended to limit the scope of the present invention in any way.

In addition, types of a functional health food, which contains the functional health food composition of the present invention for prevention or amelioration of liver steatosis, non-alcoholic fatty liver, hyperlipidemia, type 2 diabetes, and/or obesity, comprising a 2-monoacylglycerol degrading enzyme, are not particularly limited, and examples thereof can include meats, sausages, bread, chocolates, candies, snacks, confections, pizza, ramen, other noodles, gums, dairy products including ice cream, various soups, beverages, tea, drinks, alcoholic beverages, and vitamin complexes.

The health food may be used together with another food or other food additives in addition to the monoacylglycerol lipase, and may be suitably used according to a conventional method. For example, a beverage for prevention of non-alcoholic fatty liver, comprising the 2-monoacylglycerol degrading enzyme, may be prepared by adding, to the 2-monoacylglycerol degrading enzyme, calcium, an *Acanthopanax senticosus* concentrate, liquid fructose, purified water, and the like, performing mixing, filling the mixture into a bottle for drinks, performing sterilization, and then cooling the bottle to room temperature. In addition, a health supplement for prevention of liver steatosis, non-alcoholic fatty liver, hyperlipidemia, type 2 diabetes, and/or obesity, comprising the 2-monoacylglycerol degrading enzyme, may be prepared as tablets or powders by adding, to the monoacylglycerol lipase, nutritional supplement ingredients (vitamins B1, B2, B5, B6, and E, acetic acid ester, and nicotinic acid amide), oligosaccharide, 50% ethanol, and purified water, performing mixing, performing forming into granules, performing drying in a vacuum dryer, allowing the granules to pass through a 12 to 14 mesh such that uniform granules are prepared, and performing extrusion forming in an appropriate amount, or may be prepared as hard capsule products by filling the granules into hard capsules.

An effective dose of the 2-monoacylglycerol degrading enzyme contained in the health food can be used in accordance with an effective dose of the pharmaceutical composition. An amount mixed of an active ingredient may be suitably determined depending on an intended purpose such as prophylactic or therapeutic treatment. In a case of long-term ingestion intended for health and hygiene purposes or for health control purposes, the amount mixed may be equal to or less than the above-mentioned range.

In the present invention, an "individual" may be an animal, preferably a mammal, in particular, an animal including a human, and may be animal-derived cells, tissue, organ, or the like. The individual may be a patient in need of treatment.

The present invention provides a use of the 2-monoacylglycerol degrading enzyme for the manufacture of a medicament for treatment of liver steatosis, non-alcoholic fatty liver, hyperlipidemia, type 2 diabetes, and/or obesity.

Hereinafter, the present invention will be described in detail with reference to preferred examples in such a manner that those skilled in the art can easily carry out the present invention. However, the present invention may be embodied in many different modes and is not limited to examples as set forth herein.

EXAMPLES

Example 1

Production and Purification of Monoacylglycerol Lipase Protein 1-1: Production of Recombinant Vector and Recombinant Microorganism In the present invention, in order to produce a monoacylglycerol lipase protein, an *E. coli* system capable of expressing a large amount of protein, and a His-tag were used, in which open reading frame (ORF) portions of the human-derived monoacylglycerol lipase mRNA (Genebank Number: NM 001003794) and the mouse monoacylglycerol lipase mRNA (Genebank Number: NM 011844) were cloned into the pT7-HMT (His-Myc-TEVprotease) vector (Geisbrecht B V et al., Protein Expression Purif 46: 23-32, 2006).

The pT7-HMT vector is a vector which fuses a six-His tag and a target protein, and allows the resultant to be expressed in bacteria. The pT7-HMT vector has a feature that an expressed protein can be easily purified, and has an advantage that the tag can be removed, as necessary, using a TEV protease.

First, primers capable of amplifying the ORF portion (except ATG start codon) of the human or mouse-derived monoacylglycerol lipase mRNA were constructed as shown in Table 1, and construction of the primers was done by including a restriction enzyme site therein such that an amplified gene can be inserted into a vector.

TABLE 1

Primer sequence

| Gene | | Primer sequence | Restriction enzyme | SEQ ID NO |
|---|---|---|---|---|
| Human MGL | forward | 5'-GC<u>CATATG</u>ccagaggaaagttccccagg-3' | NdeI | SEQ ID NO: 1 |
| | reverse | 5'-CG<u>CTCGAG</u>tcagggtggggacgcagttc-3' | XhoI | SEQ ID NO: 2 |
| Mouse MGL | forward | 5'-GC<u>GTCGAC</u>cctgaggcaagttcacccagg-3' | SalI | SEQ ID NO: 3 |
| | reverse | 5'-CG<u>CTCGAG</u>tcagggtggacacccagctc-3' | XhoI | SEQ ID NO: 4 |

(An underlined part indicates a site where a restriction enzyme acts)

A human- or mouse-derived total RNA was extracted from fat tissue, and a polymerase chain reaction (PCR) was carried out with the extracted total RNA as a template using each of the primer pairs as shown in Table 1. As a result of identifying sequences of PCR amplification products, it was identified that the human monoacylglycerol lipase gene is represented by SEQ ID NO: 5 and the mouse-derived monoacylglycerol lipase gene is represented by SEQ ID NO: 6 (Table 2).

The amplified human- or mouse-derived monoacylglycerol lipase gene was cleaved with NdeI (Cat. No. R0111S; New England BioLabs, USA) or SalI (Cat. No. R0138S; New England BioLabs, USA), and XhoI (Cat. No. R0146S; New England BioLabs, USA), and then introduced into the pT7-HMT vector, in which the same restriction sites have been cleaved, to produce a recombinant vector. In this case, a six-His tag was made available for protein purification, and a Myc-tag was made available for protein detection using Western analysis at a later time. In addition, a design was made such that the His-Myc tags can be removed, as necessary, by applying a TEV protease.

1-2: Production and Purification of Monoacylglycerol Lipase Protein

Next, *E. coli* strain BL21 (DE3) pCodon plus (Cat. No. 230245; Agilent, USA) was transformed with the recombinant vector. The strain was inoculated into 500 ml of an LB medium containing kanamycin, chloramphenicol, and 2% ethanol, and grown until an absorbance at 600 nm reaches

TABLE 2

Sequence information for genes

| Gene | Base sequence for gene | SEQ ID NO |
|---|---|---|
| Human MGL | GC<u>CATATG</u>ccagaggaaagttccccaggcggaccccgcagagcattccctaccaggacctccct<br>cacctggtcaatgcagacggacagtacctcttctgcaggtactggaaaccacaggcacacccaaggccc<br>tcatctttgtgtcccatggagccggagagcacagtggccgctatgaagagctggctcggatgctgatgggg<br>ctggacctgctggtgttcgcccacgaccatgttggccacggacagagcgaaggggagaggatggtagtg<br>tctgacttccacgttttcgtcagggatgtgttgcagcatgtggattccatgcagaaagactaccctgggcttcc<br>tgtcttccttctgggccactccatgggaggcgccatcgccatcctcacggccgcagagaggccgggccac<br>ttcgccggcatggtactcatttcgcctctggttcttgccaatcctgaatctgcaacaactttcaaggtccttgct<br>gcgaaagtgctcaaccttgtgctgccaaacttgtccctcgggcccatcgactccagcgtgctctctcggaat<br>aagacagaggtcgacatttataactcagcccccctgatctgccgggcagggctgaaggtgcttcggcat<br>ccaactgctgaatgccgtctcacgggtggagcgcgccctcccaagctgactgtgccttcctgctgctcc<br>agggctctgccgatcgcctatgtgacagcaaaggggcctacctgctcatggagttagccaagagccagga<br>caagactctcaagatttatgaaggtgcctaccatgttctccacaaggagcttcctgaagtcaccaactccgtc<br>ttccatgaaataaacatgtgggtctctcaaaggacagccacggcaggaactgcgtccccaccctga<u>CTC<br>GAG</u>CG | SEQ ID NO: 5 |
| Mouse MGL | GC<u>GTCGAC</u>cctgaggcaagttcacccaggcgaactccacagaatgttccctaccaggacctgcctc<br>acctggtcaatgcagacggacagtacctcttttgtagatactggaagcccagtggcacacccaaggccctc<br>atctttgtgtcccatggagctggggaacactgtggccgcgttatgatgagctggctcatatgttgaaggggctg<br>gacatgctggtatttgcccatgaccatgttggccatgggcagagtgagggagaggatggtggtgtcgg<br>acttccaagtttttgtcagagatgtgctgcaacacgtggacaccatccagaaggactaccccgacgtcccca<br>tcttcctcctgggccactccatgggcggtgccatctccatcctagtggctgcagagaggccaacctactttc<br>tggcatggtcctgatttcacctctggtccttgccaatccgaatctgcatcgactttgaaggtccttgctgcca<br>aactgctcaattttgtcctgccaaatatgaccttgggcgcattgactccagcgtgctgtctcggaacaagtc<br>ggaggttgacctgtacaactctgacccactcgtctgccgagcagggctgaaggtgtgctttggcatacagc<br>tgctgaatgccgtcgcaagagtggagcgagcaatgcccaggctgacactgccattcctgctgctgcaggg<br>ttctgctgaccggctttgcgacagcaaaggtgcctacctgctcatggaatcatccccggagtcaggacaaaa<br>cactcaagatgtatgaaggtgcctatcacgtcctccacaggagcttccggaagtgaccaactccgtcctc<br>catgaagtaaactcgtgggtgtctcacaggatagcagcaggagctgggtgtccaccctga<u>CTCG<br>AGCG</u> | SEQ ID NO: 6 |

0.5 to 0.6. Then, for protein expression, IPTG was added at 1 mM, and additional culture was performed at 16° C. for 16 hours.

Bacteria were harvested by centrifugation from the culture, and suspended in a lysis buffer (50 mM Tris-Cl, pH 8.0, 500 mM NaCl, 5 mM imidazole, pH 8.0). Triton X-100 was added thereto at 1%, and then the bacteria were broken by a freezing-thawing method involving lysozyme, such that a protein homogenate was obtained. Nucleic acids were degraded by ultrasonication and centrifugation was performed. Then, His-Myc-MGL fusion proteins were allowed to be bound to a column using Ni-NTA agarose beads (Cat. No. 30210, Qiagen, USA). In order to remove endotoxins generated by lysis of bacteria, the column was washed with a 50 column volume of a washing buffer that contains Triton X-114 at 0.1%, and then washed with a 10 column volume of a washing buffer that does not contain Triton X-114.

As a result of performing several tests, elution of the protein attached to the column was carried out using EDTA rather than imidazole. The protein harvested using an elution solution (150 mM EDTA, pH 8.0, 150 mM NaCl, 50 mM Tris-Cl, pH 8.0) was then subjected to dialysis with a 200-fold volume of 50 mM Tris-Cl, pH 8.0. The resulting protein was designated "crude MGL" and used for experiments.

FIG. 6 is data, illustrating results obtained by performing SDS-PAGE after isolation and purification of a mouse-derived monoacylglycerol lipase (MGL). It was identified that a size of the mouse-derived monoacylglycerol lipase (MGL) purified in the present invention is about 33 kDa, and thus it was identified that the mouse-derived monoacylglycerol lipase has the same size as an actual mouse monoacylglycerol lipase.

A monoacylglycerol lipase to be administered into an animal was more purely purified by sequentially applying the crude MGL to HiTrap Phenyl HP, HiTrap SP, and HiTrapQ columns through a process as illustrated in FIG. 7.

Example 2

Measurement of Activity of Monoacylglycerol Lipase Protein

In the present invention, in order to measure activity of the mouse-derived monoacylglycerol lipase purified in Example 1, the isolated protein and oleoyl-rac-glycerol (Cat. No. M7765, Sigma, USA) which is a substrate of the isolated protein were reacted with each other, and glycerol liberated thereby was measured using the Glycerol assay kit (Cat. No. MAK117, Sigma, USA) with reference to a manual attached to the kit. 1 unit was defined as an amount such that 1 mole of monoacylglycerol is completely degraded for 1 hour at a condition of pH 7.4 and 37° C. In this method of measuring activity, an amount of activity was calculated with reference to a glycerol standard.

In addition, a protein concentration was measured using the Pierce™ BCA assay kit (Cat. No. 23225, ThermoFisher Scientific, USA). From this, activity per mg was calculated.

Endotoxins that may remain in the protein were measured using the Pierce™ LAL Chromogenic Endotoxin Quantitation Kit (Cat. No. 88282, ThermoFisher Scientific, USA).

The mouse-derived monoacylglycerol lipase, for which the above measurements were performed, showed the following results.

Concentration: 3 to 5 mg/ml, total 300 to 500 mg/40-liter culture
Activity: 30 to 100 units/mg protein
Endotoxin: <10 EU/ml (*EU, endotoxin unit)

Example 3

Degradation of 2-Monoacylglycerol and Obesity-Decreasing Effect

In the present example, an obesity-decreasing effect caused by a 2-monoacylglycerol degradation enzyme was identified. Specifically, a porcine pancreatic lipase (L3126, Sigma, USA) which is a 1,3-specific lipase was used as a control group and a *Candida rugosa* lipase (L1756, Sigma, USA) was selected as a non-specific lipase. Such lipases were administered into ob/ob mice (Central Lab. Animal Inc., Korea) by gavage for 7 weeks. As a result, as illustrated in FIG. 8, the *C. rugosa* lipase which is a non-specific lipase exhibited only a slight decrease in body weight as compared with the control group.

Example 4

Blood Triglyceride-Decreasing Effect Due to Administration of Monoacylglycerol Lipase In the present invention, in order to identify whether blood triglyceride is actually decreased by the mouse monoacylglycerol lipase produced in Example 1, the monoacylglycerol lipase was orally administered into mice, in which the administration into the mice was made at a unit based on the measurement results for activity in Example 2.

First, C57BL6/J mice were fasted for 4 hours or longer, and then 250 µl of olive oil was administered by a gavage method using a tube. At the same time, the control group was administered 250 µl of saline, and the experimental group was administered 250 µl of the monoacylglycerol lipase protein.

After 2 hours, mice were sacrificed and blood was collected. Then, an amount of blood triglyceride was analyzed, and measurement was performed at an absorbance of 500 nm using the Triglyceride Colorimetric Assay Kit (Cat No 10010303, Cayman, USA) according to a manual included in the kit. As a result, as illustrated in FIG. 9, it was identified that blood triglyceride was greatly decreased in a mouse group to which the monoacylglycerol lipase was administered. From this, it was identified that the monoacylglycerol lipase of the present invention completely degrades triglyceride into a fatty acid and glycerol in a digestive tract, and thus has an effect of decreasing blood absorption of triglyceride.

In addition, in the experiment as described above, measurement was performed on an hourly basis. As a result, as illustrated in FIG. 10, fat absorption was very low in the monoacylglycerol lipase-administered group as compared with the physiological saline-administered group (left side in FIG. 10), and this result was more reliably shown in an experiment where blood fat is prevented from being liberated into fat tissue by administration of tyloxopol (right side in FIG. 10).

Example 5

Measurement of Activity of Monoacylglycerol Lipase in Small Intestine

In the present example, in order to prove that the fat absorption-decreasing effect demonstrated in Example 4 is actually a result caused by action of a monoacylglycerol lipase, activity of a mouse monoacylglycerol lipase which had been orally administered was measured in the small intestine.

Mice were sacrificed 1 hour or 2 hours after administration of physiological saline or the monoacylglycerol lipase, and dissection was performed by dividing a jejunum site in the small intestine into proximal and distal portions. The dissected portions were immersed in PBS such that materials in the small intestine were allowed to elute in PBS. Activity of the monoacylglycerol lipase present therein was measured using the method as in Example 2.

As a result, as illustrated in FIG. 11, in the monoacylglycerol (MGL)-administered group, it can be observed that a shift is made from the proximal portion 1 hour after oral administration to the distal portion 2 hours after oral administration, in which total activity of the remaining protein corresponded to ⅕ to ⅒ of the orally administered protein. This means that the administered monoacylglycerol lipase is destroyed by gastric acid and gastric juice, but enzymatic activity thereof that corresponds to at least ⅒ acts in the small intestine. Therefore, this indicates that it is necessary to administer an excess amount rather than a required amount in a body for a mouse experiment. The monoacylglycerol lipase can be protected from gastric acid and gastric juice by methods such as using a coating agent at a later time.

Example 6

Effects of Delaying Triglyceride Recombination in Small Intestine Cells, Caused by Monoacylglycerol Lipase In the present example, in order to prove that the effects of delaying triglyceride absorption identified in Examples 4 and 5 actually resulted from delaying a process by which triglyceride is recombined in small intestinal cells and liberated into blood, an experiment was performed using Caco-2 cells (Cat No. HTB37, ATCC, USA) which are a human small intestine cell line. As illustrated in FIG. 12, this culture system is a system that allows a small intestinal tract side to be placed at an apical side such that fat to be digested and the mouse monoacylglycerol lipase protein produced in Example 1 are administered thereinto, and allows a blood side to be placed at a basolateral side such that an examination is performed on whether small intestinal epithelial cells therebetween are capable of absorbing the fat from a digestive tract and liberating it into blood. The Caco-2 cells were allowed to differentiate for 21 days. Impedance analysis was performed to identify whether intercellular connection after differentiation is well made such that media at both sides cannot be mixed without passing through the cells. Then, to the small intestine side, oleic acid and monooleoylglycerol were administered, and physiological saline or the monoacylglycerol lipase were administered. After being placed in an incubator for 17 hours, the medium at the blood side was recovered, and ApoB protein, which is a lipoprotein surface protein contained in the medium, was measured by an ELISA method.

As a result, as illustrated in the right graph of FIG. 12, it was identified that an amount detected of ApoB in the monoacylglycerol lipase-administered group is very low, which is a direct proof that inhibition of monoacylglycerol absorption by this enzyme can delay or decrease liberation of fat into blood by the small intestinal epithelial cells.

Example 7

Effects Obtained by Administration of Monoacylglycerol Lipase in Obesity-Induced Mice 7-1. Identification of Changes in Body Weight and Dietary Amount, and Fatty Stool Following Administration of Monoacylglycerol Lipase In the present example, it was identified whether an effect of decreasing a body weight or delaying a body weight increase is exhibited in obese ob/ob mice into which the mouse monoacylglycerol lipase produced in Example 1 has been administered for 4 weeks. For ob/ob mice (Central Lab. Animal Inc., Korea) which have slowed appetite suppression due to a mutation in a leptin gene and exhibit an obesity trait, 8-week-old mice were administered about 100 units/day of the monoacylglycerol lipase by oral gavage on a daily basis for 4 weeks. In order to synchronize feed intake with time of action of the monoacylglycerol lipase, the mice were fasted in a light cycle and then administered MGL before beginning a diet in a dark cycle (FIG. 13A).

As a result, as illustrated in FIGS. 13B and 13E, it was identified that a body weight is significantly decreased after administration of the monoacylglycerol lipase, and an effect of decreasing a total weight by 15% is exhibited after 4 weeks.

In a case where monoacylglycerol is degraded in the small intestine and fat absorption is delayed, it is possible to think about possibilities that a dietary amount can be changed, and fatty stool can be caused due to over-excretion of fat in feces. In order to examine such possibilities, a dietary amount was measured during administration of the monoacylglycerol lipase, and stool was randomly collected to examine a fat content. As a result, similar dietary amount and fecal fat content were exhibited between the MGL-administered group and the BSA-administered group (FIGS. 13C and 13D). Thus, it was identified that changes in dietary amount are not exhibited and side effects such as fatty stool are also not exhibited, due to administration of the monoacylglycerol lipase. This means that an action of inhibiting fat absorption is accompanied by promotion of energy consumption in the small intestine, and shows that such an action has a different mechanism from the way drugs such as Xenical (orlistat) suppress fat absorption.

In a case of being taken together with the results of Examples 4 to 6, the above results show that administration of the monoacylglycerol lipase into mice delays or decreases triglyceride recombination in small intestinal epithelial cells, and thus results in a decreased amount of fat which is liberated into blood and accumulated in fat tissue, thereby leading to a body weight decrease. This means that monoacylglycerol absorption is inhibited by this enzyme, and thus the monoacylglycerol lipase can be used as a therapeutic agent for obesity.

7-2. Glucose Loading Test

A glucose loading test was performed on the mice into which BSA or a monoacylglycerol lipase had been administered in Example 7-1. The mice into which the monoacylglycerol lipase had been administered were administered 1.5 mg glucose/g body weight by intraperitoneal injection. Blood was collected at 15 minutes, 30 minutes, 60 minutes, and 120 minutes before and after loading, and a blood glucose level was measured.

As a result, as illustrated in FIG. 13F, it was identified that the glucose loading test result was greatly improved. These results suggest that the monoacylglycerol lipase can be used for treatment of metabolic syndrome such as diabetes.

7-3. Effects of Ameliorating Fatty Liver and Decreasing Fat Following Administration of Monoacylglycerol Lipase The mice into which BSA or a monoacylglycerol lipase had been administered in Example 7-1 were anesthetized with ether, and the abdomen was opened. Liver and epididymal fat tissue were extracted and observed.

Figure 14A:
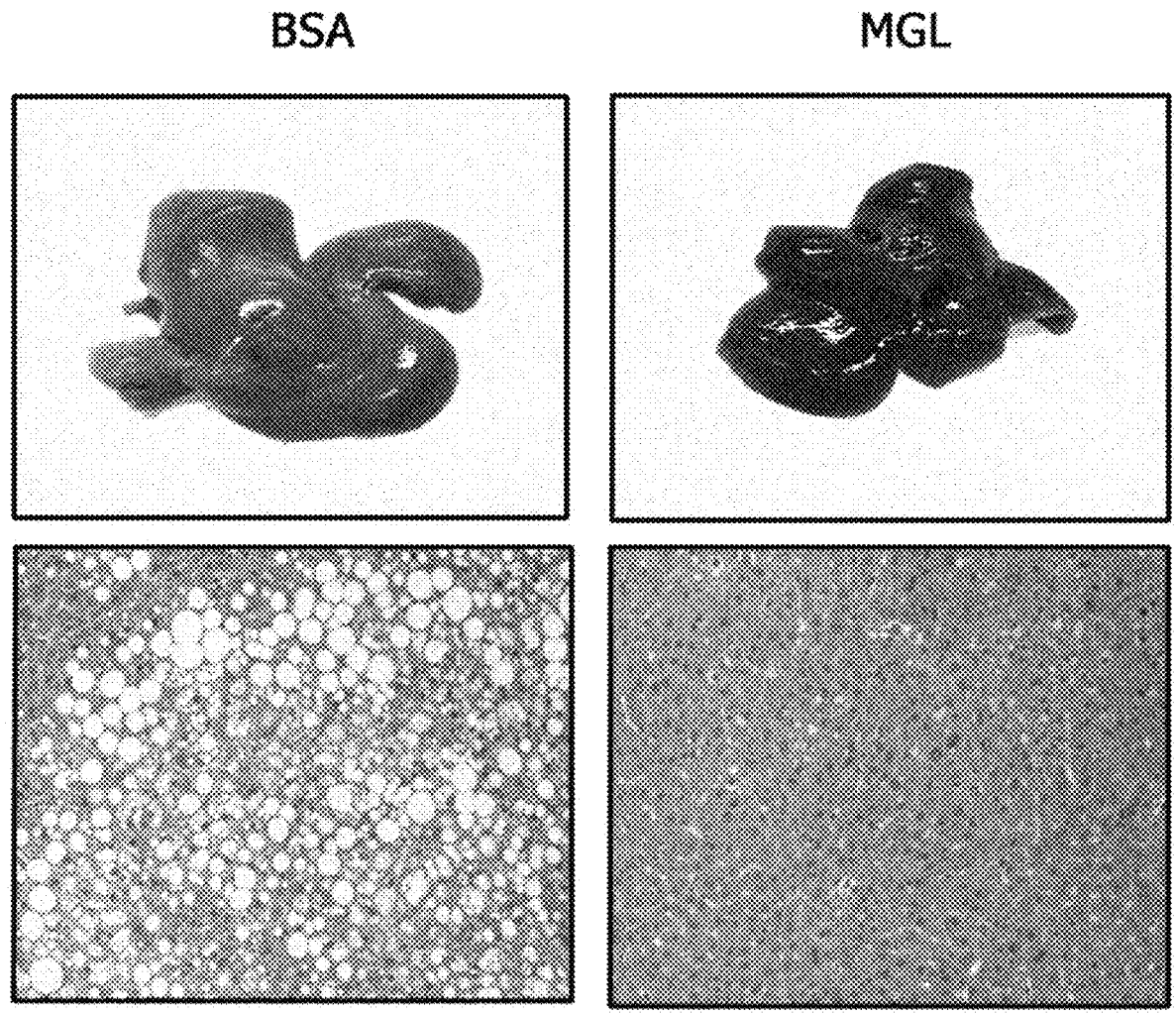
FIG. 14A illustrates appearances of livers (upper panels), which have been extracted from the mice of the BSA-administered group and the MGL-administered group after the end of the experiment of FIG. 13A, and photographs (lower panels) obtained by observing the livers using a tissue microscope.
Figure 14B:
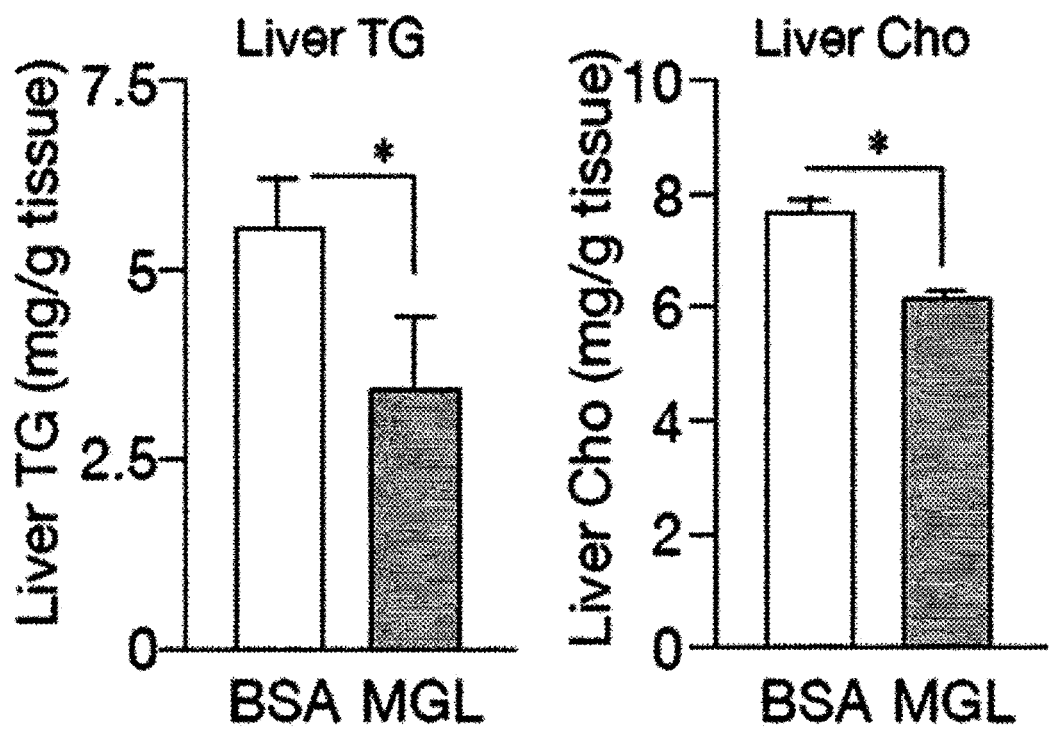
FIG. 14B graphically illustrates results obtained by measuring triglyceride and cholesterol levels in the livers of FIG. 14A.
Figure 14C:
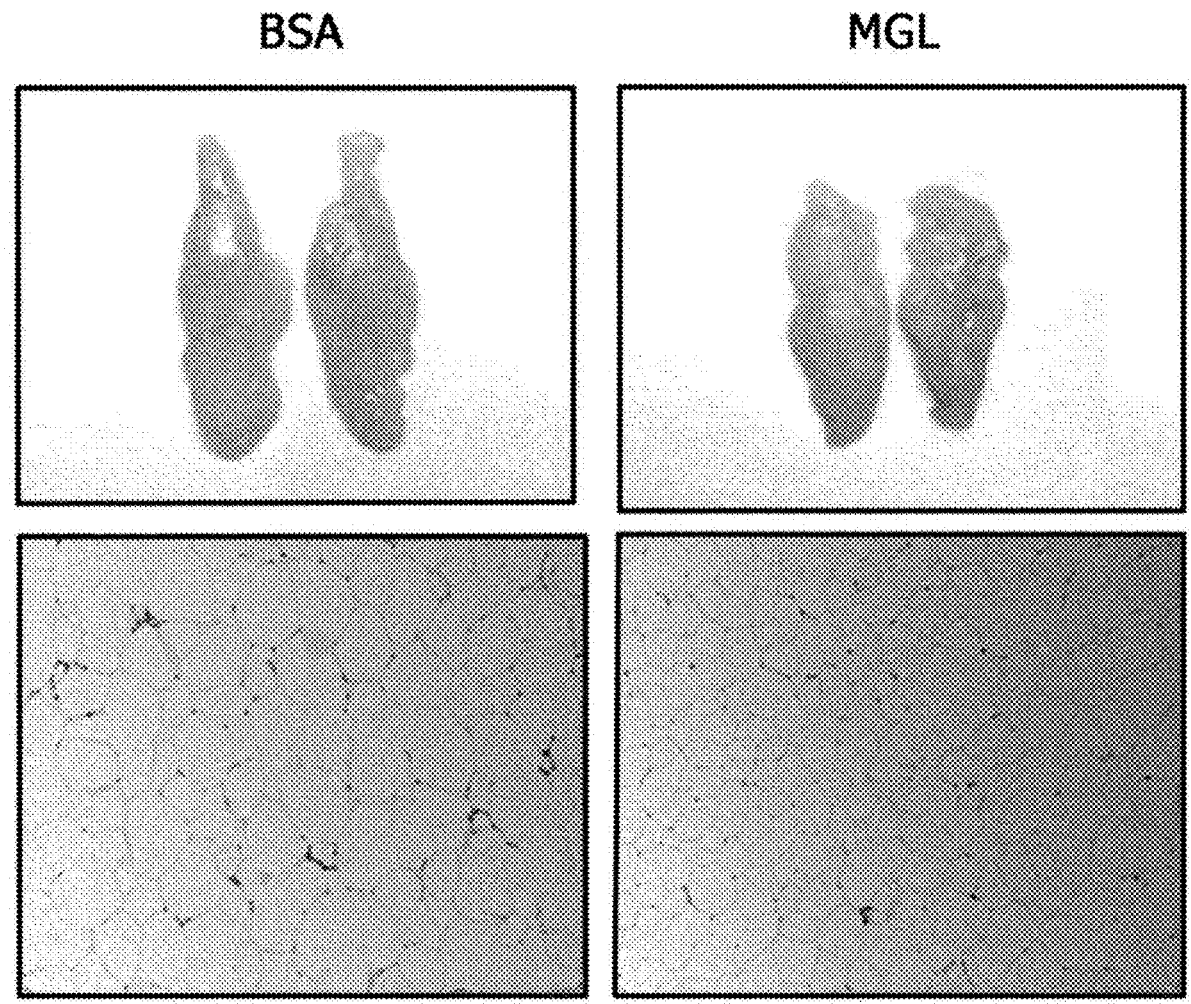
FIG. 14C illustrates appearances of epididymal fat tissue (upper panels), which has been extracted from the mice of the BSA-administered group and the MGL-administered group after the end of the experiment of FIG. 13A, and photographs (lower panels) obtained by observing the fat tissue using a tissue microscope.
Figure 14D:
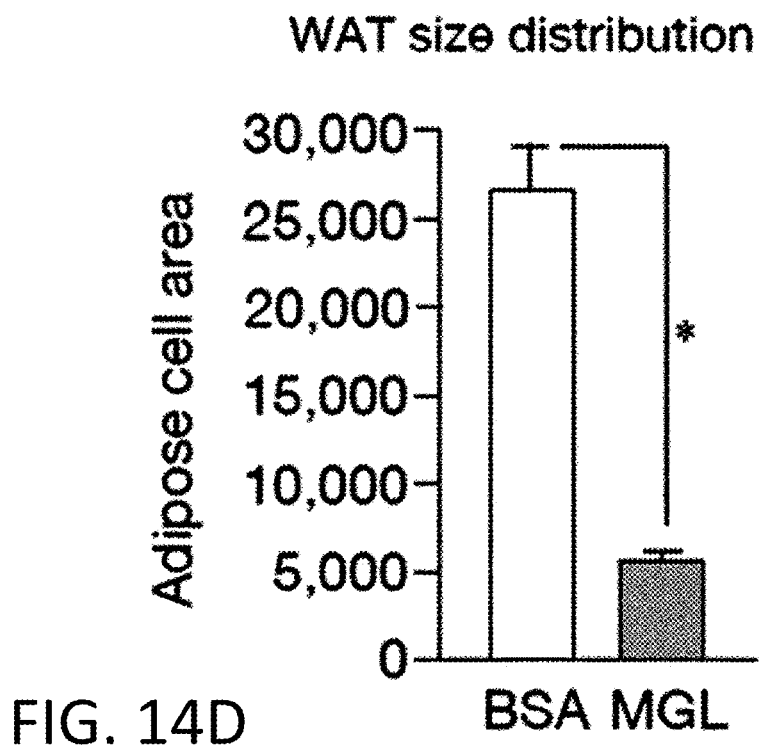
FIG. 14D graphically illustrates results obtained by measuring an average size of adipocytes in the fat tissue of FIG. 14C.

As a result, it was identified that a liver weight and a fat tissue weight are considerably decreased in the MGL-administered group (FIG. 13G), fatty liver is remarkably ameliorated (FIG. 14A), and a liver triglyceride level and a cholesterol level are also greatly decreased (FIG. 14B). In addition, following administration of MGL, it was identified that a size of the epididymal fat tissue is decreased, and a size of adipocytes is greatly decreased as a result of making an observation with a tissue microscope (FIG. 14C). FIG. 14D graphically illustrates an average size of adipocytes, in which it was possible to identify that the average size of adipocytes is remarkably smaller in the MGL-administered group than that in the BSA-administered group.

7-4. Changes in Gene Expression in Inguinal Fat

Inguinal fat, which can be considered subcutaneous fat tissue, was isolated from the mice of Example 7-3, and observation was made for changes in expression of genes for triglyceride synthesis (DGAT1, GPAT2, MGAT1, Lipin2, and Lipin3), genes for fatty acid synthesis (SCD1, FAS, and MEI), genes for fatty acid transport (CD36 and FATP1), genes for fatty acid transcription (PPARγ2, PPARα, and PGC1), and genes for fatty acid oxidation (L-CPT1, ACOX1, and UCP1).

Specifically, the mice were sacrificed, and then the inguinal fat was isolated. 100 mg of the tissue was ground and added to 1 ml of Trizol reagent (Cat. No. 15596, Invitrogen, USA), and centrifuged to remove an oil layer. A supernatant was taken, and then RNA was extracted therefrom. From 2 ug of the isolated RNA, cDNA was synthesized using SuperScript III reverse transcriptase (Cat. No. 18-080-044, Invitrogen, USA), and real-time qPCR was performed based on the synthesized cDNA using SYBR Green Master mix (Cat. No. 4309155, Applied Biosystems, USA). Expression of each gene was corrected by expression of rRNA and graphically represented. Primer sequences for detection of gene expression are as shown in Table 3 below.

TABLE 3

| Gene | | Sequence | SEQ ID NO |
|---|---|---|---|
| rRNA | forward | 5'-GCAGG TGTTT GACAA CGGCA-3' | SEQ ID NO: 9 |
| | reverse | 5'-GATGA TGGAG TGTGG CACCG-3' | SEQ ID NO: 10 |
| PPARα | forward | 5'-GTGTA CGACA AGTGT GATCG-3' | SEQ ID NO: 11 |
| | reverse | 5'-GATTT GAGGT CTGCA GTTTC-3' | SEQ ID NO: 12 |
| ACOX1 | forward | 5'-CCACA TATGA CCCCA AGACC-3' | SEQ ID NO: 13 |
| | reverse | 5'-AGGCA TGTAA CCCGT AGCAC-3' | SEQ ID NO: 14 |
| Me1 | forward | 5'-AGAGG TGTTT GCCCA TGAAC-3' | SEQ ID NO: 15 |
| | reverse | 5'-GAAGG CAGCC ATATC CTTGA-3' | SEQ ID NO: 16 |
| L-CPT1a | forward | 5'-CTCAG TGGGA GCGAC TCTTC-3' | SEQ ID NO: 17 |
| | reverse | 5'-GGCCT CTGTG GTACA CGACA-3' | SEQ ID NO: 18 |
| FATP1 | forward | 5'-CAGTG CCACC AACAA GAAGA-3' | SEQ ID NO: 19 |
| | reverse | 5'-CTGCG GTCAC GGAAA TACAT-3' | SEQ ID NO: 20 |
| CD36 | forward | 5'-TGCAC CACAT ATCTA CCAAA-3' | SEQ ID NO: 21 |
| | reverse | 5'-TTGTA ACCCC ACAAG AGTTC-3' | SEQ ID NO: 22 |
| FAS | forward | 5'-AAGCC GTTGG GAGTG AAAGT-3' | SEQ ID NO: 23 |
| | reverse | 5'-CAATC TGGAT GGCAG TGAGG-3' | SEQ ID NO: 24 |
| MGAT1 | forward | 5'-CTGGT TCTGT TTCCC GTTGT-3' | SEQ ID NO: 25 |
| | reverse | 5'-TGGGT CAAGG CCATC TTAAC-3' | SEQ ID NO: 26 |
| DGAT1 | forward | 5'-TTCCG CCTCT GGGCA TT-3' | SEQ ID NO: 27 |
| | reverse | 5'-AGAAT CGGCC CACAA TCCA-3' | SEQ ID NO: 28 |
| SCD1 | forward | 5'-TTCTC AGAAA CACAC GCCGA-3' | SEQ ID NO: 29 |
| | reverse | 5'-AGCTT CTCGG CTTTC AGGTC-3' | SEQ ID NO: 30 |
| AGPAT2 | forward | 5'-AGCGG ACAGA AGAAA CTGGA-3' | SEQ ID NO: 31 |
| | reverse | 5'-TGAAG TAGAC ACCCC CAAGG-3' | SEQ ID NO: 32 |
| LIPIN2 | forward | 5'-CCGTT GAGTC CTGGG TTAAA-3' | SEQ ID NO: 33 |
| | reverse | 5'-CATTG GAAGG CAGGT CATTT-3' | SEQ ID NO: 34 |
| LIPIN3 | forward | 5'-GCCCA TGATT CTTTC TCTGC-3' | SEQ ID NO: 35 |
| | reverse | 5'-TCTCC AGGAA AACCA CCATC-3' | SEQ ID NO: 36 |
| PPARδ2 | forward | 5'-CTCTG GGAGA TTCTC CTGTT-3' | SEQ ID NO: 37 |
| | reverse | 5'-GGTGG GCCAG AATGG CATCT-3' | SEQ ID NO: 38 |
| PGC1a | forward | 5'-TTTTT GGTGA AATTG AGGAAT-3' | SEQ ID NO: 39 |
| | reverse | 5'-CGGTA GGTGA TGAAA CCATA-3' | SEQ ID NO: 40 |
| UCP1 | forward | 5'-GGTAT AAAGG TGTCC TAGGG-3' | SEQ ID NO: 41 |
| | reverse | 5'-CAAGC TTTCT GTGGT GGCTA-3' | SEQ ID NO: 42 |

As a result, as illustrated in FIG. 15A, expression of the genes for triglyceride synthesis and the genes for fatty acid synthesis is not changed or is rather increased in the MGL-administered group, and the genes for fatty acid transport, the genes for fatty acid transcription, and the genes for fatty acid oxidation also exhibit similar patterns. One unusual thing is that expression of PGC1 and UCP1 is remarkably increased in the MGL-administered group, which means that browning of white fat is occurring and energy consumption is increased.

Example 8

Effects Obtained by Administration of Monoacylglycerol Lipase in Mice Fed High-Fat Diet 8-1. Identification of Changes in Body Weight and Dietary Amount, and Fatty Stool Following Administration of Monoacylglycerol Lipase 5-week-old C57BL/6 mice (Central Lab. Animal Inc., Korea) were fed a high-fat diet with a fat level of 45% for a total of 13 weeks. Starting from around 7 weeks after beginning the high-fat diet, the monoacylglycerol lipase produced in Example 1 was administered to identify whether an effect of decreasing a body weight or delaying a body weight increase is exhibited (FIG. 16A). As a result, as illustrated in FIGS. 16B and 16E, it was identified that a body weight is significantly decreased after administration of the monoacylglycerol lipase, and an effect of decreasing a total weight by 15% is exhibited.

In addition, as illustrated in FIGS. 16C and 16D, similar dietary amount and fecal fat content were exhibited between the MGL-administered group and the BSA-administered group. Thus, it was identified that changes in dietary amount and side effects such as fatty stool are not exhibited due to administration of the monoacylglycerol lipase.

8-2. Glucose Loading Test

A glucose loading test was performed on the mice into which BSA or a monoacylglycerol lipase had been administered in Example 8-1. The mice into which the monoacylglycerol lipase had been administered were administered 1.5 mg glucose/g body weight by intraperitoneal injection. Blood was collected at 15 minutes, 30 minutes, 60 minutes, and 120 minutes before and after loading, and a blood glucose level was measured.

As a result, as illustrated in FIG. 16F, the glucose loading test result was greatly improved. From this, it was identified once again that MGL of the present invention can be utilized as a therapeutic agent for diabetes.

8-3. Effects of Ameliorating Fatty Liver and Decreasing Fat Following Administration of Monoacylglycerol Lipase The mice into which BSA or a monoacylglycerol lipase had been administered in Example 8-1 were anesthetized with ether, and the abdomen was opened. Liver and epididymal fat tissue were extracted and observed.

As a result, it was identified that a liver weight and a fat tissue weight are considerably decreased in the MGL-administered group (FIG. 16G), and fatty liver is remarkably ameliorated as can be seen from appearances of the extracted livers observed with naked eyes and photographs obtained by staining the livers with H&E or oil-red O and making an observation using a tissue microscope (FIG. 17A). In addition, it was identified that a liver triglyceride level is remarkably decreased and a cholesterol level is also decreased (FIG. 17B), and a size of the epididymal fat tissue is decreased and a size of adipocytes is decreased as a result of observing the fat tissue using a tissue microscope (FIG. 17C). FIG. 17D graphically illustrates an average size of adipocytes, in which it was possible to identify that the average size of adipocytes is remarkably smaller in the MGL-administered group than that in the BSA-administered group.

8-4. Identification of Changes in Blood Triglyceride and Cholesterol Levels, Changes in Numerical Value for Liver, and Changes in GLP Following Administration of Monoacylglycerol Lipase Blood was collected from the mice into which BSA or a monoacylglycerol lipase had been administered in Example 8-1, and levels of triglyceride and cholesterol levels in blood were analyzed. As a result, as illustrated in FIG. 17E, it was identified that decreased blood triglyceride is exhibited and a similar blood cholesterol level to that of the BSA-administered group is exhibited, due to administration of MGL. The decreased blood triglyceride is caused by the fact that MGL of the present invention completely degrades triglyceride into a fatty acid and glycerol in a digestive tract such that blood absorption of triglyceride is decreased. From this, it was identified once again that MGL is effective as a therapeutic agent for hyperlipemia.

In addition, in view of the fact that ALT and AST which are numerical values for liver are considerably decreased in the MGL-administered group, it was found that MGL contributes to recovery of liver function (FIG. 17F). Finally, in view of the fact that the MGL-administered group exhibits no changes in blood GLP-1 which is known to be able to affect diet, it was identified once again that no changes in dietary amount are exhibited due to administration of MGL.

Example 9

Comparison of Effects Between MGL of Present Invention and Xenical

In order to make a comparison for effects between MGL of the present invention and Xenical which is currently used as a therapeutic agent for obesity, C57BL/6 mice were administered 100 units of the human MGL produced in Example 1 or 100 nmol of Xenical (orlistat, ORL, Sigma) by gavage on a daily basis for 3 weeks, and a body weight, and fecal fat and cholesterol levels were measured.

As a result, as illustrated in FIG. 18, for the body weights, MGL and ORL similarly decreased a total body weight by about 15%. However, MGL and ORL are drugs having different properties and optimal doses thereof cannot be defined. Thus, based on these results, it is not possible to compare whether MGL or ORL is superior. However, as illustrated in FIG. 18, an almost similar fecal fat level was exhibited between the MGL-administered group and the BSA-administered group, but the ORL-administered group exhibited a remarkable level of fatty stool and showed a big difference. In addition, the ORL-administered group also exhibited remarkably increased fecal cholesterol. One unusual thing is that 4 out of 5 mice in the ORL-administered group died during the 3-week administration experiment, and autopsy showed a finding that gallbladder had turned black as illustrated in FIG. 19. This is thought to be a finding of pigmented gall stone and is one of reported side effects of ORL. From the results of the present example, it can be understood that MGL is a superior anti-obesity agent and a therapeutic agent for fatty liver, in view of the fact that unlike Xenical, MGL has a considerable body weight-decreasing effect even in a range where no fatty stool is exhibited at all, and in particular, does not exhibit side effects of Xenical such as fatty stool and gallbladder lesion.

INDUSTRIAL APPLICABILITY

The composition of the present invention comprising a 2-monoacylglycerol degrading enzyme has effects of delaying fat absorption and decreasing blood absorption of triglyceride by completely degrading triglyceride into fatty acids and glycerol in a digestive tract. In a case where 2-monoacylglycerol is degraded by a 2-monoacylglycerol degrading enzyme in the digestive tract, although degraded products of the 2-monoacylglycerol are absorbed into the digestive epithelial cells, recombination thereof into triglyceride in the digestive epithelial cells can be delayed or energy consumption can be promoted during this process. Therefore, such a composition can be utilized for medical products and functional health foods for prevention, amelioration, or treatment of liver steatosis, non-alcoholic fatty liver, hyperlipidemia, type 2 diabetes, and/or obesity, and the like.

The invention claimed is:

1. A method for treating liver steatosis or non-alcoholic fatty liver, comprising:
   administering a 2-monoacylglycerol degrading enzyme to an individual in need thereof.

2. The method according to claim 1, wherein the enzyme is a lipase that specifically-degrades 2-monoacylglycerol.

3. The method according to claim 2, wherein the lipase that specifically degrades 2-monoacylglycerol is a 2-position specific lipase derived from any one selected from the group consisting of human, mouse, yeast, fungi, and bacteria.

4. The method according to claim 3, wherein the 2-position specific lipase consists of the amino acid sequence of SEQ ID NO: 7 or 8.

5. The method according to claim 4, wherein the 2-position specific lipase is expressed by a recombinant vector that contains the base sequence of SEQ ID NO: 5 or 6.

6. The method according to claim 5, wherein the 2-position specific lipase is produced by a strain transformed with the recombinant vector.

7. The method according to claim 1, wherein the 2-monoacylglycerol degrading enzyme completely degrades 2-monoacylglycerol into a fatty acid and glycerol such that an amount of 2-monoacylglycerol to be absorbed into digestive epithelial cells is decreased.

8. A method for treating hyperlipidemia or type 2 diabetes, comprising:
   administering a 2-monoacylglycerol degrading enzyme to an individual in need thereof.

9. The method according to claim 8, wherein the enzyme is a lipase that specifically or non-specifically degrades 2-monoacylglycerol.

10. The method according to claim 9, wherein the lipase that specifically degrades 2-monoacylglycerol is a 2-position specific lipase derived from any one selected from the group consisting of human, mouse, yeast, fungi, and bacteria.

11. The method according to claim 10, wherein the 2-position specific lipase consists of the amino acid sequence of SEQ ID NO: 7 or 8.

12. The method according to claim 11, wherein the 2-position specific lipase is expressed by a recombinant vector that contains the base sequence of SEQ ID NO: 5 or 6.

13. The method according to claim 12, wherein the 2-position specific lipase is produced by a strain transformed with the recombinant vector.

14. A method for treating obesity comprising:
administering a 2-monoacylglycerol degrading enzyme to an individual in need thereof.

15. The method according to claim 14, wherein the enzyme is a lipase that specifically or non-specifically degrades 2-monoacylglycerol.

16. The method according to claim 15, wherein the lipase that specifically degrades 2-monoacylglycerol is a 2-position specific lipase derived from any one selected from the group consisting of human, mouse, yeast, fungi, and bacteria.

17. The method according to claim 16, wherein the 2-position specific lipase consists of the amino acid sequence of SEQ ID NO: 7 or 8.

18. The method according to claim 17, wherein the 2-position specific lipase is expressed by a recombinant vector that contains the base sequence of SEQ ID NO: 5 or 6.

19. The method according to claim 18, wherein the 2-position specific lipase is produced by a strain transformed with the recombinant vector.

20. The method according to claim 14, wherein
the 2-monoacylglycerol degrading enzyme completely degrades 2-monoacylglycerol into a fatty acid and glycerol,
energy consumption increases due to a process by which the degraded fatty acid and glycerol are absorbed into digestive epithelial cells and re-synthesized into triglyceride, and
the increase in energy consumption is caused by consumption of three or four more ATPs as compared with a process by which monoacylglycerol and fatty acids are re-synthesized into triglyceride in the digestive epithelial cells.

* * * * *

```
                              SEQUENCE LISTING

<160> NUMBER OF SEQ ID NOS: 42

<210> SEQ ID NO 1
    <211> LENGTH: 28
    <212> TYPE: DNA
    <213> ORGANISM: Artificial Sequence
    <220> FEATURE:
    <223> OTHER INFORMATION: synthetic oligonucleotide

<400> SEQUENCE: 1
gccatatgcc agaggaaagt tccccagg                                        28

<210> SEQ ID NO 2
    <211> LENGTH: 28
    <212> TYPE: DNA
    <213> ORGANISM: Artificial Sequence
    <220> FEATURE:
    <223> OTHER INFORMATION: synthetic oligonucleotide

<400> SEQUENCE: 2
cgctcgagtc agggtgggga cgcagttc                                        28

<210> SEQ ID NO 3
    <211> LENGTH: 29
    <212> TYPE: DNA
    <213> ORGANISM: Artificial Sequence
    <220> FEATURE:
    <223> OTHER INFORMATION: synthetic oligonucleotide

<400> SEQUENCE: 3
gcgtcgaccc tgaggcaagt tcacccagg                                       29

<210> SEQ ID NO 4
    <211> LENGTH: 28
    <212> TYPE: DNA
    <213> ORGANISM: Artificial Sequence
    <220> FEATURE:
    <223> OTHER INFORMATION: synthetic oligonucleotide

<400> SEQUENCE: 4
cgctcgagtc agggtggaca cccagctc                                        28

<210> SEQ ID NO 5
    <211> LENGTH: 925
    <212> TYPE: DNA
    <213> ORGANISM: Homo sapiens

<400> SEQUENCE: 5
gccatatgcc agaggaaagt tccccaggc ggaccccgca gagcattccc taccaggacc      60
tccctcacct ggtcaatgca gacgacagt acctcttctg caggtactgg aaacccacag     120
gcacacccaa ggccctcatc tttgtgtccc atggagccgg agagcacagt ggccgctatg    180
aagagctggc tcggatgctg atggggctgg acctgctggt gttcgcccac gaccatgttg    240
```

```
gccacggaca gagcgaaggg gagaggatgg tagtgtctga cttccacgtt ttcgtcaggg    300
atgtgttgca gcatgtggat ccatgcaga aagactaccc tgggcttcct gtcttccttc    360
tgggccactc catgggaggc gccatcgcca tcctcacggc cgcagagagg ccgggccact    420
tcgccggcat ggtactcatt tcgcctctgg ttcttgccaa tcctgaatct gcaacaactt    480
tcaaggtcct tgctgcgaaa gtgctcaacc ttgtgctgcc aaacttgtcc ctcgggccca    540
tcgactccag cgtgctctct cggaataaga cagaggtcga catttataac tcagaccccc    600
tgatctgccg ggcagggctg aaggtgtgct tcggcatcca actgctgaat gccgtctcac    660
gggtggagcg cgcccctccc aagctgactg tgcccttcct gctgctccag ggctctgccg    720
atcgcctatg tgacagcaaa ggggcctacc tgctcatgga gttagccaag agccaggaca    780
agactctcaa gatttatgaa ggtgcctacc atgttctcca caaggagctt cctgaagtca    840
ccaactccgt cttccatgaa ataaacatgt gggtctctca aggacagcc acggcaggaa     900 ctgcgtcccc accctgactc gagcg                                          925
```

<210> SEQ ID NO 6
<211> LENGTH: 925
<212> TYPE: DNA
<213> ORGANISM: Mus musculus

<400> SEQUENCE: 6

```
gcgtcgaccc tgaggcaagt tcacccaggc gaactccaca gaatgttccc taccaggacc     60
tgcctcacct ggtcaatgca gacggacagt acctcttttg tagatactgg aagcccagtg    120
gcacacccaa ggccctcatc tttgtgtccc atggagctgg gaacactgt ggccgttatg     180 atgagctggc tcatatgttg aaggggctgg acatgctggt atttgcccat gaccatgttg    240
gccatgggca gagtgaggga gagaggatgg tggtgtcgga cttccaagtt tttgtcagag    300
atgtgctgca acacgtggac accatccaga aggactaccc cgacgtcccc atcttcctcc    360
tgggccactc catgggcggt gccatctcca tcctagtggc tgcagagagg ccaacctact    420
tttctggcat ggtcctgatt tcacctctgg tccttgccaa tccggaatct gcatcgactt    480
tgaaggtcct tgctgccaaa ctgctcaatt ttgtcctgcc aaatatgacc ttggggcgca    540
ttgactccag cgtgctgtct cggaacaagt cggaggttga cctgtacaac tctgacccac    600
tcgtctgccg agcagggctg aaggtgtgct ttggcataca gctgctgaat gccgtcgcaa    660
gagtggagcg agcaatgccc aggctgacac tgccattcct gctgctgcag ggttctgctg    720
accggctttg cgacagcaaa ggtgcctacc tgctcatgga atcatcccgg agtcaggaca    780
aaacactcaa gatgtatgaa ggtgcctatc acgtcctcca cagggagctt ccggaagtga    840
ccaactccgt cctccatgaa gtaaactcgt gggtgtctca caggatagca gcagcaggag    900
ctgggtgtcc accctgactc gagcg                                          925
```

<210> SEQ ID NO 7
<211> LENGTH: 304
<212> TYPE: PRT
<213> ORGANISM: Homo sapiens

<400> SEQUENCE: 7

Met Pro Glu Glu Ser Ser Pro Arg Arg Thr Pro Gln Ser Ile Pro Tyr
1               5                   10                  15

Gln Asp Leu Pro His Leu Val Asn Ala Asp Gly Gln Tyr Leu Pro Cys
                20                  25                  30

Arg Tyr Trp Lys Pro Thr Gly Thr Pro Lys Ala Leu Ile Pro Val Ser
            35                  40                  45

His Gly Ala Gly Glu His Ser Gly Arg Tyr Glu Glu Leu Ala Arg Met
 50                  55                  60

Leu Met Gly Leu Asp Leu Leu Val Pro Ala His Asp His Val Gly His
 65                  70                  75                  80

Gly Gln Ser Glu Gly Glu Gly Arg Met Val Val Ser Asp Pro His Val
                85                  90                  95

Pro Val Arg Asp Val Leu Gln His Val Asp Ser Met Gln Lys Asp Tyr
            100                 105                 110

Pro Gly Leu Pro Val Pro Leu Leu Gly His Ser Met Gly Gly Ala Ile
            115                 120                 125

Ala Ile Leu Thr Ala Ala Glu Arg Pro Gly His Pro Ala Gly Met Val
        130                 135                 140

Leu Ile Ser Pro Leu Val Leu Ala Asn Pro Glu Ser Ala Thr Thr Pro
145                 150                 155                 160

Lys Val Leu Ala Ala Lys Val Leu Asn Leu Val Leu Pro Asn Leu Ser
                165                 170                 175

Leu Gly Pro Ile Asp Ser Ser Val Leu Ser Arg Asn Lys Thr Glu Val
            180                 185                 190

Asp Ile Tyr Asn Ser Asp Pro Leu Ile Cys Arg Ala Gly Leu Lys Val
        195                 200                 205

Cys Pro Gly Ile Gln Leu Leu Asn Ala Val Ser Arg Val Glu Arg Ala
        210                 215                 220

Leu Pro Lys Leu Thr Val Pro Pro Leu Leu Gln Gly Ser Ala Asp
225                 230                 235                 240

Arg Leu Cys Asp Ser Lys Gly Ala Tyr Leu Leu Met Glu Leu Ala Lys
                245                 250                 255

Ser Gln Asp Lys Thr Leu Lys Ile Tyr Glu Gly Ala Tyr His Val Leu
            260                 265                 270

His Lys Glu Leu Pro Glu Val Thr Asn Ser Val Pro His Glu Ile Asn
        275                 280                 285

Met Trp Val Ser Gln Arg Thr Ala Thr Ala Gly Thr Ala Ser Pro Pro
290                 295                 300

<210> SEQ ID NO 8
<211> LENGTH: 303
<212> TYPE: PRT
<213> ORGANISM: Mus musculus

<400> SEQUENCE: 8

Met Pro Glu Ala Ser Ser Pro Arg Arg Thr Pro Gln Asn Val Pro Tyr
1               5                   10                  15

Gln Asp Leu Pro His Leu Val Asn Ala Asp Gly Gln Tyr Leu Pro Cys
            20                  25                  30

Arg Tyr Trp Lys Pro Ser Gly Thr Pro Lys Ala Leu Ile Pro Val Ser
            35                  40                  45

His Gly Ala Gly Glu His Cys Gly Arg Tyr Asp Glu Leu Ala His Met
 50                  55                  60

Leu Lys Gly Leu Asp Met Leu Val Pro Ala His Asp His Val Gly His
 65                  70                  75                  80

Gly Gln Ser Glu Gly Glu Arg Met Val Val Ser Asp Pro Gln Val Pro
                85                  90                  95

Val Arg Asp Val Leu Gln His Val Asp Thr Ile Gln Lys Asp Tyr Pro
            100                 105                 110

-continued

Asp Val Pro Ile Pro Leu Leu Gly His Ser Met Gly Ala Ile Ser
    115                 120                 125

Ile Leu Val Ala Ala Glu Arg Pro Thr Tyr Pro Ser Gly Met Val Leu
130                 135                 140

Ile Ser Pro Leu Val Leu Ala Asn Pro Glu Ser Ala Ser Thr Leu Lys
145                 150                 155                 160

Val Leu Ala Ala Lys Leu Leu Asn Pro Val Leu Pro Asn Met Thr Leu
                165                 170                 175

Gly Arg Ile Asp Ser Ser Val Leu Ser Arg Asn Lys Ser Glu Val Asp
            180                 185                 190

Leu Tyr Asn Ser Asp Pro Leu Val Cys Arg Ala Gly Leu Lys Val Cys
        195                 200                 205

Pro Gly Ile Gln Leu Leu Asn Ala Val Ala Arg Val Glu Arg Ala Met
    210                 215                 220

Pro Arg Leu Thr Leu Pro Pro Leu Leu Gln Gly Ser Ala Asp Arg
225                 230                 235                 240

Leu Cys Asp Ser Lys Gly Ala Tyr Leu Leu Met Glu Ser Ser Arg Ser
                245                 250                 255

Gln Asp Lys Thr Leu Lys Met Tyr Glu Gly Ala Tyr His Val Leu His
            260                 265                 270

Arg Glu Leu Pro Glu Val Thr Asn Ser Val Leu His Glu Val Asn Ser
        275                 280                 285

Trp Val Ser His Arg Ile Ala Ala Gly Ala Gly Cys Pro Pro
    290                 295                 300

```
<210> SEQ ID NO 9
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 9
gcaggtgttt gacaacggca                                             20

<210> SEQ ID NO 10
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 10
gatgatggag tgtggcaccg                                             20

<210> SEQ ID NO 11
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 11
gtgtacgaca agtgtgatcg                                             20

<210> SEQ ID NO 12
<211> LENGTH: 20
<212> TYPE: DNA
<213> ORGANISM: Artificial Sequence
<220> FEATURE:
```

<223> OTHER INFORMATION: synthetic oligonucleotide

<400> SEQUENCE: 12
gatttgaggt ctgcagtttc                                                    20

<210> SEQ ID NO 13
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 13
ccacatatga ccccaagacc                                                    20

<210> SEQ ID NO 14
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 14
aggcatgtaa cccgtagcac                                                    20

<210> SEQ ID NO 15
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 15
agaggtgttt gcccatgaac                                                    20

<210> SEQ ID NO 16
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 16
gaaggcagcc atatccttga                                                    20

<210> SEQ ID NO 17
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 17
ctcagtggga gcgactcttc                                                    20

<210> SEQ ID NO 18
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 18
ggcctctgtg gtacacgaca                                                    20

```
<210> SEQ ID NO 19
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 19
cagtgccacc aacaagaaga                                                     20

<210> SEQ ID NO 20
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 20
ctgcggtcac ggaaatacat                                                     20

<210> SEQ ID NO 21
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 21
tgcaccacat atctaccaaa                                                     20

<210> SEQ ID NO 22
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 22
ttgtaacccc acaagagttc                                                     20

<210> SEQ ID NO 23
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 23
aagccgttgg gagtgaaagt                                                     20

<210> SEQ ID NO 24
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 24
caatctggat ggcagtgagg                                                     20

<210> SEQ ID NO 25
<211> LENGTH: 20
<212> TYPE: DNA
<213> ORGANISM: Artificial Sequence
<220> FEATURE:
<223> OTHER INFORMATION: synthetic oligonucleotide
```

```
<400> SEQUENCE: 25
ctggttctgt ttcccgttgt                                               20

<210> SEQ ID NO 26
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 26
tgggtcaagg ccatcttaac                                               20

<210> SEQ ID NO 27
<211> LENGTH: 17
<212> TYPE: DNA
<213> ORGANISM: Artificial Sequence
<220> FEATURE:
<223> OTHER INFORMATION: synthetic oligonucleotide

<400> SEQUENCE: 27
ttccgcctct gggcatt                                                  17

<210> SEQ ID NO 28
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 28
agaatcggcc cacaatcca                                                19

<210> SEQ ID NO 29
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 29
ttctcagaaa cacacgccga                                               20

<210> SEQ ID NO 30
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 30
agcttctcgg ctttcaggtc                                               20

<210> SEQ ID NO 31
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 31
agcggacaga agaaactgga                                               20

<210> SEQ ID NO 32
<211> LENGTH: 20
```

```
<212> TYPE: DNA
<213> ORGANISM: Artificial Sequence
<220> FEATURE:
<223> OTHER INFORMATION: synthetic oligonucleotide

<400> SEQUENCE: 32
agcggacaga agaaactgga                                              20

<210> SEQ ID NO 33
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 33
ccgttgagtc ctgggttaaa                                              20

<210> SEQ ID NO 34
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 34
cattggaagg caggtcattt                                              20

<210> SEQ ID NO 35
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 35
gcccatgatt ctttctctgc                                              20

<210> SEQ ID NO 36
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 36
tctccaggaa aaccaccatc                                              20

<210> SEQ ID NO 37
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 37
ctctgggaga ttctcctgtt                                              20

<210> SEQ ID NO 38
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 38
```

```
ggtgggccag aatggcatct                                              20

<210> SEQ ID NO 39
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 39
tttttggtga aattgaggaa t                                            21

<210> SEQ ID NO 40
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 40
cggtaggtga tgaaaccata                                              20

<210> SEQ ID NO 41
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 41
ggtataaagg tgtcctaggg                                              20

<210> SEQ ID NO 42
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 42
caagctttct gtggtggcta                                              20
```